United States Patent
Borreani et al.

(10) Patent No.: US 11,523,803 B2
(45) Date of Patent: Dec. 13, 2022

(54) METHOD FOR CONTROLLING IMAGE APPEARANCE FEATURES IN ULTRASOUND SYSTEM, IMAGE APPEARANCE FEATURE CONTROL USER INTERFACE OPERATING ACCORDING TO THE SAID METHOD AND ULTRASOUND SYSTEM COMPRISING SAID USER INTERFACE

(71) Applicant: ESAOTE SpA, Genoa (IT)

(72) Inventors: Giampaolo Borreani, Genoa (IT); Roberto Pesce, Savona (IT); Luca Bombino, Rapallo (IT)

(73) Assignee: Esaote S.p.A., Genoa (IT)

( * ) Notice: Subject to any disclaimer, the term of this patent is extended or adjusted under 35 U.S.C. 154(b) by 95 days.

(21) Appl. No.: 16/473,499

(22) PCT Filed: Jan. 2, 2017

(86) PCT No.: PCT/IB2017/050001
§ 371 (c)(1),
(2) Date: Jun. 25, 2019

(87) PCT Pub. No.: WO2018/122620
PCT Pub. Date: Jul. 5, 2018

(65) Prior Publication Data
US 2020/0146657 A1 May 14, 2020

(51) Int. Cl.
*A61B 8/00* (2006.01)
*A61B 8/08* (2006.01)
(52) U.S. Cl.
CPC .............. *A61B 8/54* (2013.01); *A61B 8/4488* (2013.01); *A61B 8/467* (2013.01); *A61B 8/5207* (2013.01)
(58) Field of Classification Search
CPC ......... A61B 8/54; A61B 8/4488; A61B 8/467; A61B 8/5207; G01S 7/52071;
(Continued)

(56) References Cited

U.S. PATENT DOCUMENTS

| 2004/0006266 A1* | 1/2004 | Ustuner | A61B 8/08 600/407 |
| 2014/0221832 A1* | 8/2014 | El-Zehiry | G16H 40/63 600/437 |

(Continued)

FOREIGN PATENT DOCUMENTS

| EP | 3081166 A1 | 10/2016 |
| WO | 2005059586 A1 | 6/2005 |

OTHER PUBLICATIONS

European Search Report and Written Opinion dated Sep. 27, 2017, which issued in corresponding PCT Patent Application No. PCT/IB2017/050001.

*Primary Examiner* — Joseph M Santos Rodriguez
*Assistant Examiner* — Kaitlyn E Sebastian
(74) *Attorney, Agent, or Firm* — Dickinson Wright PLLC

(57) ABSTRACT

Controlling an image appearance in ultrasound system comprises: providing a set of image appearance feature control parameters, each of which relates to an image appearance feature according to a pre-defined relation between a value scale of the said image appearance feature control parameter and an image appearance related to a certain condition of the corresponding image appearance feature; generating a function between the value of each image feature control parameter and the value of the standard workflow setting parameters of a combination of standard workflow setting parameters influencing the said image appearance feature; and varying automatically the value of the one or more of the standard workflow setting parameters of the combination of standard workflow setting parameters influencing an image appearance feature as a function of a variation of the value of the corresponding image appearance feature control parameters for obtaining the requested image appearance feature variation.

32 Claims, 15 Drawing Sheets

(58) Field of Classification Search
CPC ............. G01S 7/52084; G01S 7/52098; G01S 7/5206; G01S 7/52063
See application file for complete search history.

(56) References Cited

U.S. PATENT DOCUMENTS

2015/0327838 A1\* 11/2015 Francis ................ A61B 8/5276
 600/450
2017/0090571 A1\* 3/2017 Bjaerum .............. A61B 8/4254
2017/0156698 A1\* 6/2017 Park .................... G06F 3/04847

\* cited by examiner

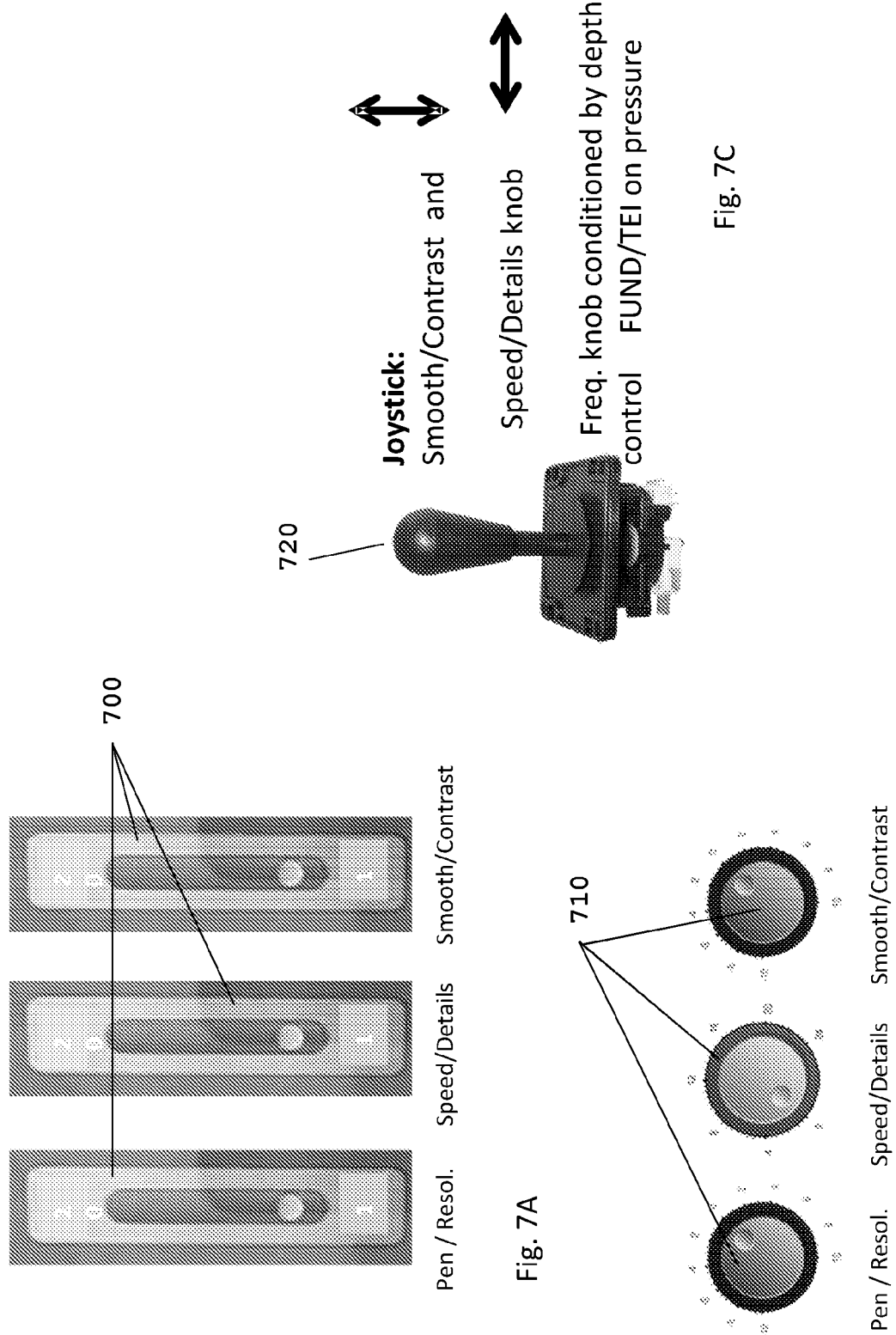

METHOD FOR CONTROLLING IMAGE APPEARANCE FEATURES IN ULTRASOUND SYSTEM, IMAGE APPEARANCE FEATURE CONTROL USER INTERFACE OPERATING ACCORDING TO THE SAID METHOD AND ULTRASOUND SYSTEM COMPRISING SAID USER INTERFACE

BACKGROUND

Example embodiments of the present disclosure relate to a method for controlling image appearance features in ultrasound systems by setting the values of workflow setting parameters having an influence on the final image appearance in such a way that one or more image appearance features are set in desired condition of providing the said final image appearance.

Current user interfaces of standard ultrasound systems are based on controls which are not logically correlated to final image appearance. It is the operator/user who has to translate his experience/know-how in proper system's settings adapted to the real-time scan needs. The current image end user controls are based on standard workflow setting parameters which are more related to the physics of the imaging process than to the final appearance of the images visualized on the display. For doctors or paramedical operators which have a limited knowledge of the system workflow and of the physical processes governing the ultrasound imaging, it is often difficult to influence the image appearance by controlling the values of the said standard workflow setting parameters. Furthermore many different standard workflow setting parameters have an influence on a certain image appearance feature so that the operator has to control several different setting parameters in order to modify the image appearance.

Furthermore, operators with limited skills of the system workflow may incur in reaching a "bad tuning" configuration of the setting parameters which provide for a desired image appearance but which are not optimal or detrimental for obtaining quality images.

Therefore the final aim is to provide a smart method for controlling image appearance features in ultrasound system, an image appearance feature control user interface operating according to the said method and an ultrasound system comprising said user interface not requiring a specific skill on more technical and physical aspects of medical ultrasound imaging which is normally out of usual background of final users.

SUMMARY

In the description and in the following claims the term Standard workflow setting parameters refers and comprises all the parameters which can be set by the user through a user interface for adjusting according to special needs the operative condition of an ultrasound system. Particularly this terms comprises and refers to settings related to the physics of the imaging process and the imaging device and which do not have a direct relation with an image appearance feature but influence nevertheless the said image appearance features alone or in combination with other parameters.

In accordance with example embodiments in the present disclosure, a method is provided for controlling an image appearance in ultrasound system, the said method comprising:

providing a set of image appearance feature control parameters, each one of which is related to an image appearance feature according to a pre-defined relation between a value scale of the said image appearance feature control parameter and an image appearance related to a certain condition of the corresponding image appearance feature;

generating a relation between the value of each image appearance feature control parameter and the value of the standard workflow setting parameters of a combination of standard workflow setting parameters influencing the said image appearance feature;

varying automatically the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance feature control parameter;

visualizing of the image with the requested image appearance feature.

According to the said method steps the number of controls is considerably reduced. Each image appearance feature control parameter is directly related to an image appearance feature, like for example smoothness, contrast, resolution, penetration, details, speed and other possible appearance features of the ultrasound image to be visualized on screen.

Each image appearance feature control parameter is expressed as a function of a combination of one or more of the standard workflow setting parameters which have an influence on the image appearance feature associated with the said image appearance feature control parameter.

According to an embodiment the said functional relation of the image appearance feature control parameter with a combination of standard workflow setting parameters is factory defined.

Still according to another embodiment, the said factory defined functional relation of the image appearance feature control parameter with a combination of standard workflow setting parameters may be modified by the user.

The value of each image appearance feature control parameter is associated with a scale or a field of values ranging from a minimum value to a maximum value. The scale may be linear or logarithmic or set according to a different metric function, the minimum value and the maximum values corresponding to a certain extreme condition of the image appearance feature related to the image appearance feature control parameter a function being defined relating the values of the image appearance feature control parameter to the conditions of appearance of the corresponding image appearance feature.

According to an embodiment herein each standard workflow setting parameter of the combination of standard workflow setting parameters defining the image appearance feature control parameter is related to the image appearance feature control parameter by a specific function which may be different from the one of the other standard workflow setting parameters of the combination.

According to an embodiment herein the factory definition steps of the method comprise the following steps:

defining a set of independent image appearance features and assigning to each image appearance feature a related image appearance feature control parameter;

defining the image appearance feature control parameter of each image appearance feature as a function of a combination of one or more ultrasound system standard workflow setting parameters related to the physics of the imaging process and which influence the corresponding image appearance feature;

for each image appearance feature, generating a correlation between the variation of the image appearance relatively to the image appearance feature and the variation of the value of the corresponding image appearance feature control parameter;
for each image appearance feature, generating a correlation between the values of the image appearance feature control parameter and the values of the said standard workflow setting parameters of the combination of the said standard workflow setting parameters by empirically or experimentally or numerically
defining for each standard workflow setting parameter a function relating the values of the said image appearance feature control parameter to the values of the standard workflow setting parameter or
a database or a look-up table consisting in an array of the values of the corresponding image appearance feature control parameter and the values of each of the standard workflow setting parameters defining the image appearance feature associated with a value of the image appearance feature control parameter which values are empirically or experimentally determined;
the said function being used or the said database or the said look-up table being addressable and readable for:
relating the value of each image appearance feature control parameter to the value of the standard workflow setting parameters of a combination of standard workflow setting parameters influencing the said image appearance feature;
varying automatically the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance feature control parameter.

The final step is naturally printing, saving and or visualizing the image with the requested image appearance feature settings.

In relation to the above disclosed method, considering the controls of the image appearance features based directly on the standard workflow setting parameters, these setting parameters forms a multidimensional space of data with multiple possibilities of combination of the values of the standard workflow setting parameters contributing to determining a certain image appearance. Defining a new kind of image appearance feature control parameters which are directly related to the appearance of the image in relation to certain appearance features and relating functionally the said control parameters to a combination of the sole standard workflow imaging parameters having an influence on the corresponding image appearance feature represents a definition of a sub space having a reduced number of dimensions.

According to a further improvement the said function relating the values of the said image appearance feature control parameter to the values of the standard workflow setting parameter of the combination of standard workflow setting parameter describing the image appearance feature control parameter is determined numerically by calculating the best fit curve of empirically or experimentally measured relation between different image appearance conditions of an image appearance feature, the corresponding value of the image appearance feature control parameter and the corresponding values of the standard workflow setting parameters of the combination of standard workflow setting parameter describing the image appearance feature control parameter.

According to a specific non limiting embodiment of the present method image appearance feature control parameters are set for the following image appearance features combination:
Penetration-resolution ratio
speed-detail ratio;
smooth-contrast ratio.

According to still another specific non limiting embodiment,
the penetration-resolution ratio image appearance feature control parameter is a function of the following standard workflow setting parameters: frequency, number of transmit pulses;
the speed-detail ratio image appearance feature control parameter is a function of the following standard workflow setting parameters: Image field of view, Persistence, Line density, Number of view lines and XView-details;
the smooth-contrast ratio image appearance feature control parameter is a function of the following standard workflow setting parameters: Dymanic compression, dynamic range, enhancement, graymap settings, MView settings, Xview-balance, Xview-Smooth, XView-enhancement.

The specific embodiment disclosed above shows that it is possible of reducing a 14 dimensional space of standard workflow setting parameters in a three dimensional sub space of image appearance feature control parameters being expressed as combinations of a plurality of the said standard workflow setting parameters and being univocally related to determining the ratio between two complementary image appearance features such as in the example discussed above Penetration-resolution ratio, speed-detail ratio, smooth-contrast ratio.

According to still another embodiment which may be provided in combination of each one of the above disclosed embodiments, the method may provide the steps of providing a control input organ operable by the user for each control parameter, for setting the value of the corresponding image appearance feature control parameter according to a desired setting of the image appearance feature, which control input organ has two extreme positions each one being related to one of two image appearance feature defined by the same combination of standard workflow setting parameters and which image appearance feature are complementary one to the other so that at one end position a first of the said two image appearance feature prevails and at the opposite end position a second of the said two image appearance feature prevails and in the intermediate positions of the control input organ a combination of the two image appearance features is generated, which combination has different ratio of the said image appearance features as a function of the position of the control input organ between the two extreme end positions.

According to still another embodiment which may be provided in a combination of any of the further embodiments, the method for controlling image appearance features in ultrasound systems comprises the steps of
modifying the value of at least one of the standard workflow setting parameters of the combination of standard workflow setting parameters defining an image appearance feature control parameter corresponding to a certain value of the said image appearance feature control parameter with respect to a factory defined value;
determining a continuity/discontinuity threshold for the modified value relatively to the function describing the relation between the image appearance feature control parameter and the said standard workflow setting parameter;

determining by comparing with the said continuity/discontinuity threshold if the modified values determine a discontinuity in the function describing the relation between the image appearance feature control parameter and the said standard workflow setting parameter, and defining a new function describing the relation between the image appearance feature control parameter and the said standard workflow setting parameter by an approximation curve passing through the end points of the value range for the said standard workflow setting parameter and through the said modified value of the said standard workflow setting parameter;

substituting the previous function with the new function and using the new function for determining the values of the standard workflow setting parameter as a function of the image appearance feature control parameter.

According to an embodiment herein for the definition of a new function an approximation by a parabola coefficient method is carried out.

Example embodiments of the present disclosure relate also to an image appearance feature control user interface operating according to the said method.

According to an embodiment of the said image appearance feature control interface in ultrasound system, comprises:

a control input organ operable by the user univocally associated with at least one image appearance feature, for setting the value of the corresponding image appearance feature control parameter according to a desired setting of the corresponding image appearance feature;

the said control input organ having two extreme positions each one being related to at least one of two extreme conditions of the said image appearance feature while in the intermediate positions of the control input organ between the said two extreme positions continuously or discretely varying image appearance is set relating to the said image appearance feature as a function of the variation of the value of the corresponding image appearance feature control parameter caused by varying the position of the said control input organ between the said two extreme positions;

the image appearance feature control parameter being a function of a combination of standard workflow setting parameters of the ultrasound scanner which influence the corresponding image appearance feature such that by operating the control input organ in order to vary the image appearance feature determined by a certain value of the image appearance control parameter the corresponding values of the combination of the standard workflow setting parameters determining the requested condition of the image appearance feature are automatically set.

A further embodiment herein which may be combined with the previous embodiment, relates to an image appearance feature control interface in which the same control input organ is associated for controlling two or more image complementary appearance features whose image appearance feature control parameters are the function of an identical combination of standard workflow setting parameter of the ultrasound system and coupling the said image appearance features control parameter to a single image appearance feature control parameter influencing the said image appearance features;

defining a correlation function between the corresponding image appearance feature control parameter and the control input organ position between the two extreme positions such at one end position of the control input organ a first of the said two image appearance features prevails, and at the opposite end position a second of the said two image appearance features prevails, and in the intermediate positions of the control input organ a combination of the two image appearance features is generated, which combination has different ratio of the said image appearance features as a function of the position of the control input organ between the two extreme end positions.

According to a specific embodiment the image appearance feature control interface is provided with a control input organ for one or more of the following couple of complementary image appearance features:
Penetration-resolution ratio
speed-detail ratio;
smooth-contrast ratio.

According to a further improvement of the above embodiment, the penetration-resolution ratio image appearance feature control parameter is a function of the following standard workflow setting parameters: frequency, number of transmit pulses Alternatively or in combination the speed-detail ratio image appearance feature control parameter is a function of the following standard workflow setting parameters: Image field of view, Persistence, Line density, Number of view lines and XView-details Alternatively or in combination the smooth-contrast ratio image appearance feature control parameter is a function of the following standard workflow setting parameters: Dynamic compression, dynamic range, enhancement, graymap settings, MView settings, Xview-balance, Xview-Smooth, XView-enhancement.

According to still another embodiment herein the which the control input organs are electronical, electrostatically or mechanically hand operable physical control organs such as cursors or knobs or the like, or the control input organs are virtual, hand, gesture or voice operable organs or combination thereof.

In a preferred embodiment the control input organs are graphically represented organs on a touch screen interface.

In the above case according to an embodiment the user interface comprises a processor unit and a touch screen display controlled by the said processing unit. The processing unit executing a software configured for printing on screen the icons representing the control organs and for animating the said control organs to change their aspect by operating them through the touch screen interface, thereby generating input signals for setting values for the image appearance feature control parameter associated with the control organ.

Many different alternatives are currently known for generating a digital virtual control interface and each one of these available alternatives may be used for the control organs.

According to an embodiment herein the image control user interface comprises further A processor configured to carry out the following tasks computing a function describing the relation of the values of the corresponding image appearance feature control parameter and the values of each of the standard workflow setting parameters defining the image appearance feature associated with a value of the image appearance feature control parameter which function is numerically determined by approximating empirically or experimentally determined values or determining the values of each of the standard workflow setting parameters defining the image appearance feature associated with a value of the image appearance feature control parameter by addressing a database or a look-up table saved in a memory of the processor and comprising an array of the values of the corresponding image appearance feature control parameter and the values of each of the standard workflow setting parameters defining the image appearance feature associated with a value of the image appearance feature control parameter which values are empirically or experimentally determined, for determining the value of each image appearance feature control parameter to the value of the standard workflow setting parameters of a combination of standard workflow setting parameters influencing the said image appearance feature;

varying automatically the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance control parameter;

visualizing of the image with the requested image appearance feature setting.

According to still another embodiment which may be provided in a combination of any of the further embodiments, the image control user interface for controlling image appearance features in ultrasound systems comprises also input control organs of the standard workflow setting parameters for modifying the value of at least one of the standard workflow setting parameters of the combination of standard workflow setting parameters defining an image appearance feature control parameter corresponding to a certain value of the said image appearance feature control parameter with respect to a factory defined value; And a processor configured for storing a continuity/discontinuity threshold for the modified value relatively to the function describing the relation between the image appearance feature control parameter and the said standard workflow setting parameter and determining by comparing with the said continuity/discontinuity threshold if the modified values determine a discontinuity in the function describing the relation between the image appearance feature control parameter and the said standard workflow setting parameter, and for numerically computing a new function describing the relation between the image appearance feature control parameter and the said standard workflow setting parameter by an approximation curve passing through the end points of the value range for the said standard workflow setting parameter and through the said modified value of the said standard workflow setting parameter;

the processor further substitutes the previous function with the new function and uses the new function for determining the values of the standard workflow setting parameter as a function of the image appearance feature control parameter.

According to an embodiment herein for the definition of a new function an approximation by a parabola coefficient method is carried out by the processor.

The invention relates also to an ultrasound system comprising an image appearance feature control interface according to one or more of the above disclosed embodiments and operating according to one or more of the method steps disclosed above.

According to an embodiment herein the ultrasound imaging system comprises:

an ultrasound probe including an array of transducer elements transforming electric input signals into acoustic transmit signals and transforming acoustic echo signals into electric receive signals;

a transmit beamformer generating the driving input signals for the transducer elements according to a transmit scheme for driving the transducer array to transmit a plurality of transmit beams from an array transducer;

a receive beamformer including a receive signals processing unit configured to process the echo signals received in response to the transmit beams to produce a plurality of receive lines of echo signals;

a signal processing unit processing the echo signals in order to extract image data from the said echo signals an image generation unit producing an image using the said image data;

an image display and an image user input interface for visualizing data images and messages from the ultrasound system to the user and for inputting control settings or selection of operative conditions and or imaging modes or other input data by the user to the ultrasound system, the said image user interface comprising further:

a control input organ operable by the user univocally associated with at least one image appearance feature of the image printed on the image display, for setting the value of the corresponding image appearance feature control parameter according to a desired setting of the corresponding image appearance feature;

the said control input organ having two extreme positions each one being related to at least one of two extreme conditions of the said image appearance feature while in the intermediate positions of the control input organ between the said two extreme positions continuously or discretely varying image appearance is set relating to the said image appearance feature as a function of the variation of the value of the corresponding image appearance feature control parameter caused by varying the position of the said control input organ between the said two extreme positions;

the image appearance feature control parameter being a function of a combination of standard workflow setting parameters of the ultrasound scanner which influence the corresponding image appearance feature such that by operating the control input organ in order to vary the image appearance feature determined by a certain value of the image appearance control parameter the corresponding values of the combination of the standard workflow setting parameters determining the requested image appearance feature are automatically set.

According to a further embodiment which may be provided in combination with the previous one the ultrasound imaging system is provided with electronically, electrostatically or mechanically hand operable physical control organs such as cursors or knobs or the like, or the control input organs are virtual, hand, gesture or voice operable organs.

According to an alternative embodiment the control input organs are graphically represented organs on a touch screen interface.

Still according to a further embodiment which may be provided in combination with one or more of the above described ones, the ultrasound imaging system comprises, A processor to which the user interface is connected, the processor being configured to alternatively computing a function describing the relation of the values of the corresponding image appearance feature control parameter and the values of each of the standard workflow setting parameters defining the image appearance feature associated with a value of the image appearance feature control parameter which function is numerically determined by approximating empirically or experimentally determined values or determining the values of each of the standard workflow setting parameters defining the image appearance feature associated with a value of the image appearance feature control parameter by addressing a database or a look-up table saved in a memory of the processor and comprising an array of the values of the corresponding image appearance feature control parameter and the values of each of the standard workflow setting parameters defining the image appearance feature associated with a value of the image appearance feature control parameter which values are empirically or experimentally determined, for determining the value of each image appearance feature control parameter related to the value of the standard workflow setting parameters of a combination of standard workflow setting parameters influencing the said image appearance feature;

varying automatically the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance control parameter;

visualizing of the image with the requested image appearance feature setting.

According to still another embodiment which may be provided in a combination of any of the further embodiments, the ultrasound imaging system comprises an image control user interface for controlling image appearance features in ultrasound systems having additionally input control organs of the standard workflow setting parameters, the said input control organs allowing to modifying the value of at least one of the standard workflow setting parameters of the combination of standard workflow setting parameters defining an image appearance feature control parameter corresponding to a certain value of the said image appearance feature control parameter with respect to a factory defined value; And a processor communicating with the input control organ and configured for reading the modified value of the standard workflow setting parameter;

storing a continuity/discontinuity threshold for the modified value relatively to the function describing the relation between the image appearance feature control parameter and the said standard workflow setting parameter and determining by comparing with the said continuity/discontinuity threshold if the modified values determine a discontinuity in the function describing the relation between the image appearance feature control parameter and the said standard workflow setting parameter, and executing a software for numerically computing a new function describing the relation between the image appearance feature control parameter and the said standard workflow setting parameter by an approximation curve passing through the end points of the value range for the said standard workflow setting parameter and through the said modified value of the said standard workflow setting parameter;

the processor further substitutes the previous function with the new function, stores the new function in a memory and uses the new function for determining the values of the standard workflow setting parameter as a function of the image appearance feature control parameter.

According to an embodiment herein for the definition of a new function an approximation by a parabola coefficient method is carried out by the processor.

According to a further aspect of example embodiments of the present disclosure, a method for generating an image appearance control end user interface in ultrasound systems is provided.

A generic embodiment of the said method comprises the following steps:

defining a set of independent image appearance features, which may be as non limiting example one or more of the following: contrast-smooth, penetration-resolution, speed-detail;

analysing the dependency of each of the said image appearance features from one or more ultrasound system standard workflow setting parameters related to the physics of the imaging process, which may be as non-limiting example one or more of the following: Persistence, Image Field of view, Enhancement, Xview-Smooth, Xview-Enhancement, Mview settings, Number of view lines, Xview Details, Dynamic Range, XView-Balance, Frequency. Line density, Gray Map settings, Dynamic compression, fundamental Mode, Tei Mode;

for each image appearance feature defining an image appearance feature control parameter as a function of the combination of one or more of the said standard workflow setting parameters resulting from the dependency analysis of the previous step;

for each image appearance feature, generating a correlation between the variation of the image appearance relatively to the image appearance feature and the variation of the value of the corresponding image appearance feature control parameter;

for each image appearance feature, generating a correlation between the values of the image appearance feature control parameter and the values of the said standard workflow setting parameters of the combination of the said standard workflow setting parameters defining the said image appearance feature control parameter.

According to the above embodiment image appearance features are individuated which may be of interest of the user and each of these feature has been univocally related to an image appearance feature control parameter which variation directly influences the image appearance feature to which it is associated. Controlling this unique parameter, the corresponding values of the standard workflow setting parameters which has an influence of the image appearance feature associated with the image appearance feature control parameter are automatically set without any need of the operator to have an insight in the basic mechanism of the imaging process and of the system workflow.

According to a further improvement, the method for generating an image appearance control end user interface comprises the further step of determining image appearance features which image appearance feature control parameters are the function of an identical combination of standard workflow setting parameter of the ultrasound system and coupling the said image appearance features control parameter to a single image appearance feature control parameter influencing the said image appearance features.

According to still a further feature which may be provided in combination with one or more of the previous ones the method for generating an image appearance control end user interface comprises the further step of assigning a control input organ operable by the user for each control parameter for setting the value of the corresponding image appearance feature control parameter according to a desired setting of the image appearance feature, which control input organ has two extreme positions each one being related to one of two image appearance features defined by the same combination of standard workflow setting parameters and which image appearance feature are complementary to each other so that at one end position a first of the said two image appearance features prevails, and at the opposite end position a second of the said two image appearance features prevails, and in the intermediate positions of the control input organ a combination of the two image appearance features is generated, which combination has different ratio of the said image appearance features as a function of the position of the control input organ between the two extreme end positions.

According to still another embodiment herein each standard workflow setting parameter of the combination defining an image appearance feature control parameter is related to the image appearance feature control parameter by a function which may be different for each of the said standard workflow setting parameters of the said combination.

According to a further embodiment herein the said function may be a best fit curve between the experimentally or empirically determined values of the said standard workflow setting parameters and the corresponding image appearance feature control parameter.

Still according to a further embodiment the method for generating an image appearance control end user interface comprises the steps of
generating a multidimensional space of standard setting parameters, having the number of dimensions corresponding to the number of the different standard setting parameters; the said multidimensional space being defined by a corresponding multidimensional array of data of the values of the said standard setting parameters and the combination of the said values in relation to the different image appearance features;
defining each image appearance feature control parameter as a sub-space contained in the said multidimensional space having a reduced number of dimensions each one corresponding to an image appearance feature control parameter; the said sub space being determined by the combination of standard workflow setting parameters influencing the image appearance feature associated with an image appearance feature control parameter and consisting in the sub array of the multidimensional array comprising the values of the said standard workflow setting parameters of the said combination of standard workflow setting parameters influencing the image appearance feature associated with an image appearance feature control parameter.

Further improvements and the related advantages will be described in the following detailed description of example embodiments of the present disclosure.

BRIEF DESCRIPTION OF THE DRAWINGS

FIGS. 7A, 7B, 7C and 7D show different embodiments of the input control organs of the image appearance feature control user interface according to the present disclosure.

DETAILED DESCRIPTION OF EXAMPLE EMBODIMENTS

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1A:
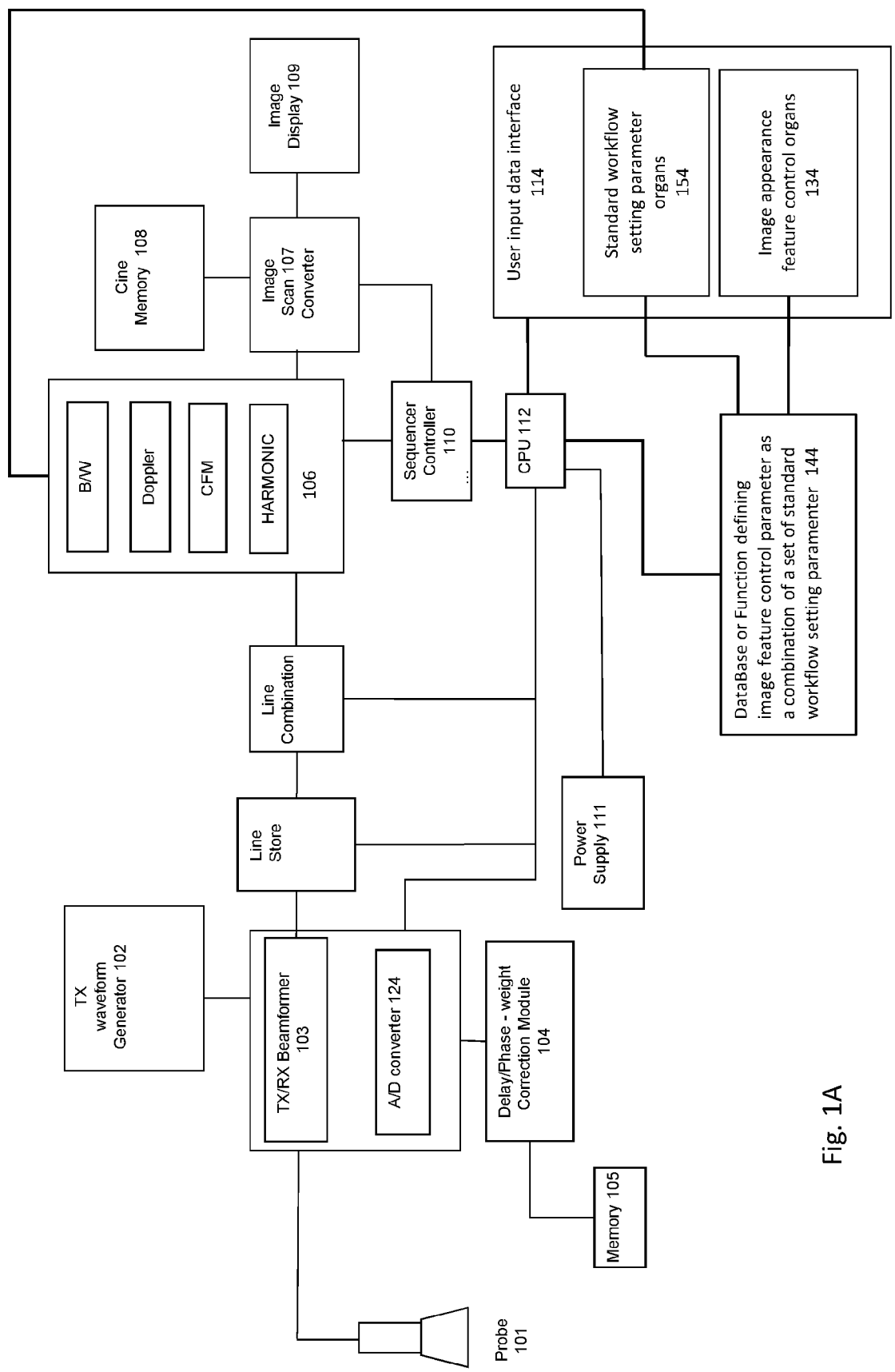
FIG. 1A illustrates a block diagram of an ultrasound system according to an embodiment.

FIG. 1A illustrates a high-level block diagram of an ultrasound system implemented in accordance with embodiments herein. Portions of the system (as defined by various functional blocks) may be implemented with dedicated hardware, analog and/or digital circuitry, and/or one or more processors operating program instructions stored in memory. Additionally, or alternatively, all or portions of the system may be implemented utilizing digital components, digital signal processors (DSPs) and/or field programmable gate arrays (FPGAs) and the like. The blocks/modules illustrated in FIG. 1 can be implemented with dedicated hardware (DPSs, FPGAs, memories) and/or in software with one or more processors.

The ultrasound system of FIG. 1 includes one or more ultrasound probes 101. The probe 101 may include various transducer array configurations, such as a one dimensional array, a two dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a beamformer 103. The beamformer 103 includes a transmit (TX) beamformer and a receive (RX) beamformer that are jointly represented by TX/RX beamformer 103. The TX and RX portions of the beamformer may be implemented together or separately. The beamformer 103 supplies transmit signals to the probe 101 and performs beamforming of "echo" receive signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, Doppler imaging, color Doppler imaging, pulse-inversion transmit techniques, contrast-based imaging, M-mode imaging and the like. Additionally, or alternatively, the transmit signals may include single or multi-line transmit, shear wave transmit signals and the like.

The beamformer 103 performs beamforming of the transmit beams in order to focalize the transmit beams progressively along different adjacent lines of sight covering the entire ROI. The beamformer performs also beamforming upon received echo signals to form beamformed echo signals in connection to pixel locations distributed across the region of interest. For example, in accordance with certain embodiments, the transducer elements generate raw analog receive signals that are supplied to the beamformer. The beamformer adjusts the delays to focus the receive signal along one or more select receive beams and at one or more select depths within the region of interest (ROI). The beamformer adjusts the weighting of the receive signals to obtain a desired apodization and profile. The beamformer applies weights and delays to the receive signals from individual corresponding transducers of the probe. The delayed, weighted receive signals are then summed to form a coherent receive signals.

The beamformer 103 includes (or is coupled to) an A/D converter 124 that digitizes the receive signals at a selected sampling rate. The digitization process may be performed before or after the summing operation that produces the coherent receive signals.

Optionally, a dedicated sequencer/timing controller 110 may be programmed to manage acquisition timing which can be generalized as a sequence of firings aimed at select reflection points/targets in the ROI. The sequence controller 110 manages operation of the TX/RX beamformer 103 in connection with transmitting ultrasound beams and measuring image pixels at individual line of sight (LOS) locations along the lines of sight. The sequence controller 110 also manages collection of receive signals.

One or more processors 106 perform various processing operations as described herein.

In accordance with embodiments herein the beamformer 103 includes an output that is configured to be coupled to an ultrasound probe 101 and sends signals to the transducer elements of the probe 101.

According to an embodiment herein the sequencer 110 controls the beamformer in order to generate and transmit a plurality of transmit beams In accordance with embodiments herein, the beamformer 103 includes an input that is configured to be coupled to an ultrasound probe 101 and receive signals from transducers of the ultrasound probe 101. The memory 105 stores time delays to align contributions of reflection signals received by the transducers of the array of the probe 101 from the reflectors in the ROI. The memory 105 also stores phase corrections to correct phase differences of the receive signals contributions for each transducer element.

A delay/phase correction (DPC) module 104 is coupled to the memory 105 and provides various delays and corrections to the beamformer 103. For example, the DPC module 104 directs the beamformer 103 to apply time delay and phase correction to the receive signals to form delayed receive signals. The beamformer 103 then sums, in a coherent manner, the delayed receive signals to obtain a coherent receive signal in connection with a reflection point or a reflection target.

Optionally, the memory 105 may store a common phase shift correction in connection with multiple channels. Different phase shift corrections may be stored in connection with various corresponding channels in the case of multiple receive signals are received along a common receive line position but due to a certain number of different transmit beams each one having a laterally shifted transmit center line and an aperture or width encompassing the receive line position. The memory 105 may also store weights such as apodization weights and/or retrospective transmit beamforming (RTB) weights.

As explained herein, the beamformer 103 (circuitry) is configured to apply contemporaneously to each receive signal contribution of each transducer element from a reflection point a beamforming focalization delay and a phase shift equalization delay so called RTB delay. The said beamforming focalization delay being calculated basing on the time of arrival of the said signal contribution to a transducer element when traveling from the reflection point to the said transducer element and the said phase shift equalization delay being determined according to the difference in phase of the wave front reaching the reflecting point relatively to the phase of the wave fronts reaching the same reflecting point and being of further transmitted beams which are laterally shifted each other.

Optionally, the memory 105 may store a pre-calculated table, where the pre-calculated table comprises real times of arrival of the receive signals relative to a predetermined reflection point. Optionally, the processor 106 may be configured to calculate real times of arrival of the receive signals relative to a predetermined reflection point. Optionally the memory 105 may store a pre-calculated table, where the pre-calculated table comprises pre-calculated phase shift equalization delays to be applied contemporaneously to the beamforming focalization delays to the receive signals of a receive line along a certain line of sight or a certain receive line position deriving from a certain number of transmit beams being differently laterally shifted relatively to the said receive line position, the number of the said transmit beams being set by setting a certain aperture or lateral width of the said transmit beams. Optionally the memory 105 may store a pre-calculated table of the said phase shift equalization delays which are pre-calculated for one or more of different transmit beams apertures or widths.

Optionally, the processor 106 may be configured to calculate the said phase shift equalization delays for one or more of different transmit beams apertures or widths.

Optionally, the beamformer 103 circuitry may further comprise an adder unit for adding the beamforming delays and the phase shift equalization delays (RTB delays) for the receive signal contributions deriving from each reflecting point.

In accordance with certain embodiments, at least a portion of the beamforming process may be implemented by the processor 106 (e.g., in connection with software RTB beamforming). For example, the memory 105 may store beamforming related program instructions that are implemented by the processor 106 to contemporaneously apply beamforming delays and phase shift equalization delays to the receive signals.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations. Optionally, the processor 106 and/or CPU 112 may filter the first and second displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown.

A control CPU module 112 is configured to perform various tasks such as implementing the user/interface and overall system configuration/control. In case of fully software implementation of the ultrasound signal path, the processing node usually hosts also the functions of the control CPU.

A power supply circuit 111 is provided to supply power to the various circuitry, modules, processors, memory components, and the like. The power supply 111 may be an A.C. power source and/or a battery power source (e.g., in connection with portable operation).

The user input data interface 114 is provided with controls for selecting and setting different working or configuration options of the ultrasound system. According to an embodiment of the present disclosure, the user interface has a standard interface comprising organs 154 for setting standard workflow setting parameters by the operator/user for influencing the image output of the system.

The user interface 114 is also provided with an image appearance feature control interface comprising control organs 134 for setting the said parameters.

According to an embodiment the standard workflow setting parameter control interface 154 and the image appearance feature control parameter interface 134 may be activated alternatively or in combination.

In a memory 144 there is stored a database in the form of a data tarry or of a look up table or a function defining each image appearance feature control parameter by a combination of one or more of the standard workflow setting parameters having an influence on the image appearance feature associated with the image appearance feature control parameter.

When an input control organ of an image appearance feature control parameter is operated for changing the condition of the related image appearance feature in an image, the CPU 112 or a dedicated processor for controlling the interface reads the input value of the image appearance feature control parameter set by the input control organ 134. Basing on this value of the image appearance feature control parameter the CPU 112 or the dedicated processor (not shown) determines the corresponding values of the standard workflow setting parameters providing an influence on the image appearance feature of an image corresponding to the one required by the setting of the image appearance feature control parameter by using the database or the look up table or the function stored in memory 144. These values are then automatically set and fed to the system for example the processor 106.

Each image appearance feature control parameter is individuated by analysing the image appearance feature and assigning to the said features one control parameter. Furthermore, the said image appearance feature control parameter is univocally associated with a combination of the standard workflow setting parameters which influence the image appearance feature associated with the image appearance feature control parameter.

As a further improvement some image appearance features may be complementary and may be influenced by the same combination of standard workflow setting parameters. In this case the image appearance features are coupled and a single image appearance feature control parameter is assigned to the two complementary image appearance features.

Figure 1B:
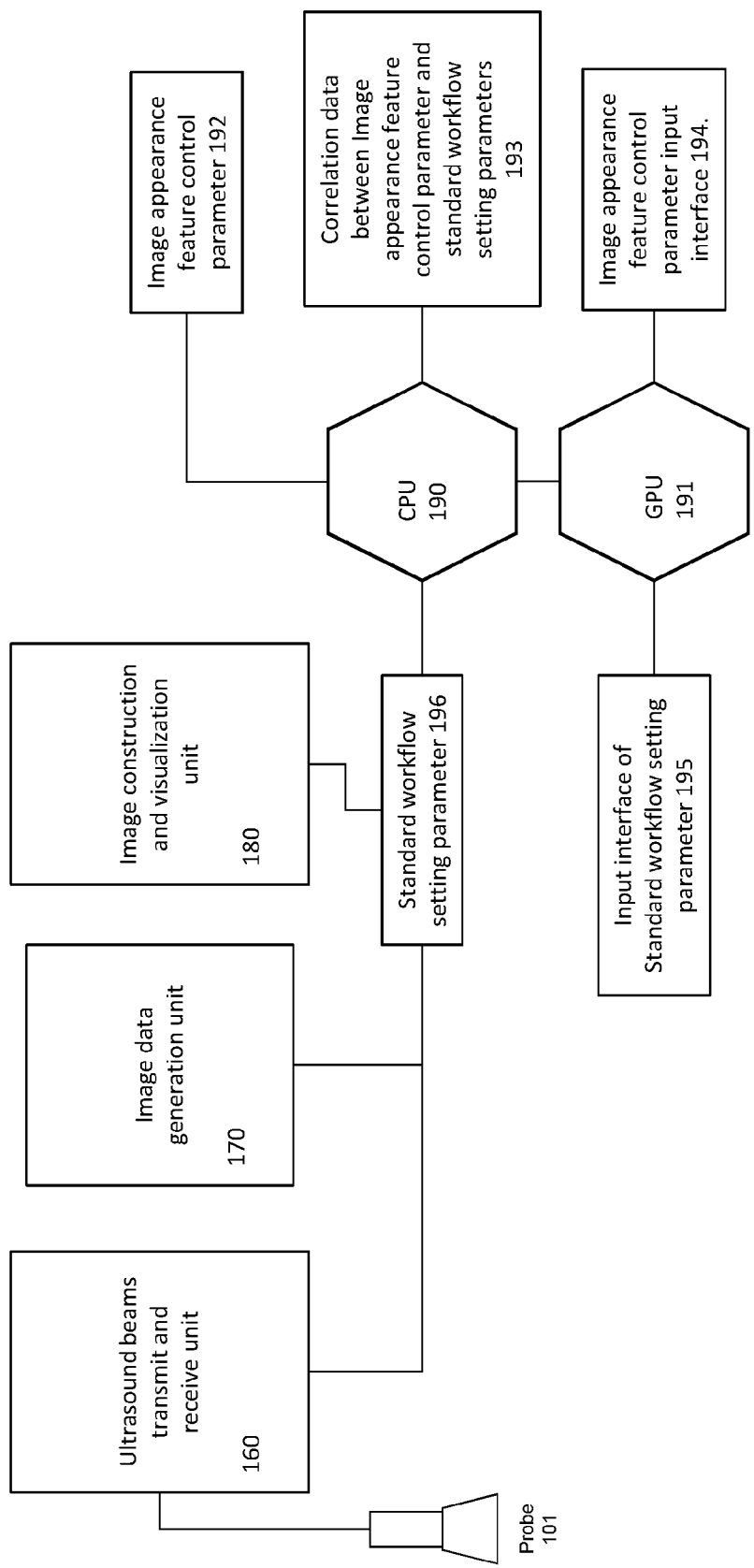
FIG. 1B illustrates a block diagram of an ultrasound system according to an embodiment.

FIG. 1B shows a further high level block diagram of the ultrasound system according to example embodiments of the present disclosure. Similarly to the embodiment of FIG. 1A a probe 101 is driven for transmitting and receiving ultrasound signals by an ultrasound receive and transmit unit 160. The ultrasound beam receive and transmit unit 160 is responsible for generating the signals driving the probe for transmitting the ultrasound beams, for applying focalization delays according to different imaging techniques, for modulating the signals with different functions according to different coding techniques or chirp techniques and for selecting the frequency of the ultrasound transmit beam.

In relation to the received signals the unit 160 is responsible for applying focalization delays according to different techniques, apodization weights, phase shift corrections, for encoding, demodulating, coherent summing, filtering of the received signals according to the different imaging techniques.

The signals processed by the unit 160 are further processed in the image data generation unit, in which image data is extracted from the received signals, furthermore in the unit 180 an image is reconstructed from the extracted image data and prepared for being printed on a screen, a printer or other devices and/or for being stored.

A user interface allows to set different operative parameter of the ultrasound system for operating according to different imaging modes and for influencing the image appearance in relation to selected image appearance features. The user interface comprises a CPU 190 which is configured to execute instructions coded in program for managing the user interface. In a memory 192 the image appearance feature control parameters are stored for different image appearance features. In a further memory 193 correlation data between each image appearance feature control parameter and one or more standard workflow setting parameters having an influence on the image appearance feature associated with the image appearance feature control parameter are stored. This correlation data may be in the form of a function relating the values of the image appearance feature control parameter to the values of each of the standard workflow setting parameters influencing the image appearance feature associated with the image appearance feature control parameter. Alternatively, the said correlation data may be in the form of a database or of a look-up table.

The graphic processing unit (GPU) 191 or alternatively the same CPU 190 execute instructions coded in a program for managing an image appearance feature control parameter input interface 194. This interface 194 provides organs from inputting values of one or more image appearance feature control parameters. These organs may be alternatively physical controls, mechanical, electric or electronic controls which are operated by hand like cursors, knobs or the like or virtual control organs which are represented on display screen and which may be operated by a mouse or similar device or directly by the hand of the user in the case the screen is a touchscreen.

Alternatively, or in parallel the GPU manages an input interface 195 of the standard workflow setting parameters which has similar control organs as the ones of the image appearance feature control parameters of the interface 194 according to one or more of the different embodiments described above.

Basing on the input values of the input interface 194 for the image appearance feature control parameters, the GPU 191, read the input data and transmit these data to the CPU 190. The CPU 190 determines the values of each one of the standard workflow setting parameters of the combination of these parameters defining the image appearance feature control parameter by reading the correlation data in the memory 193 and automatically sets the said standard workflow setting parameters values by a unit 196 connected to the different units 160, 170 and 180 which are responsible for executing processes influenced by the said standard workflow setting parameters.

Figure 4:
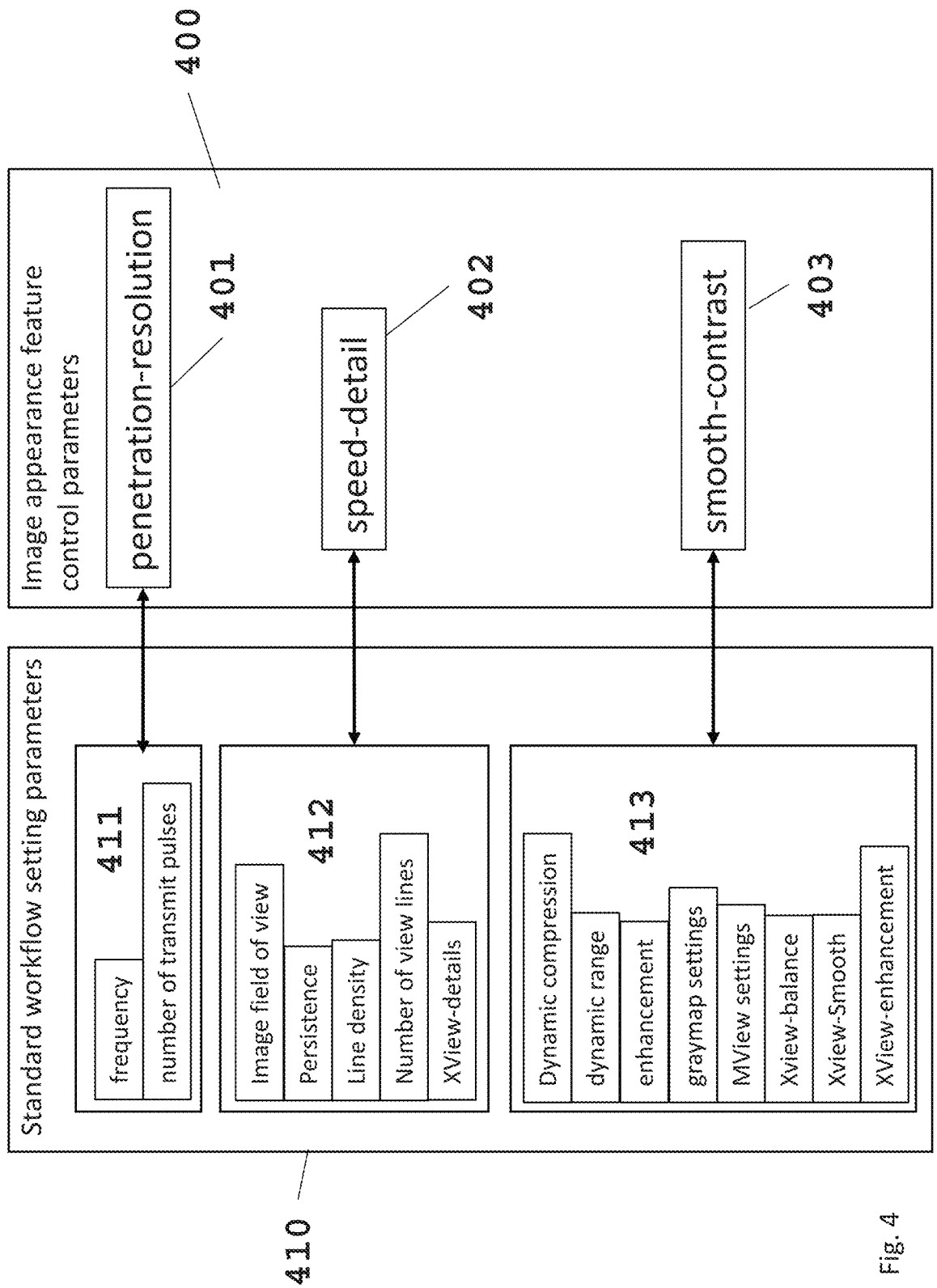
FIG. 4 illustrates an example of relation between three image appearance feature control parameter to the standard workflow setting parameters according to an embodiment of the present disclosure.
Figure 5:
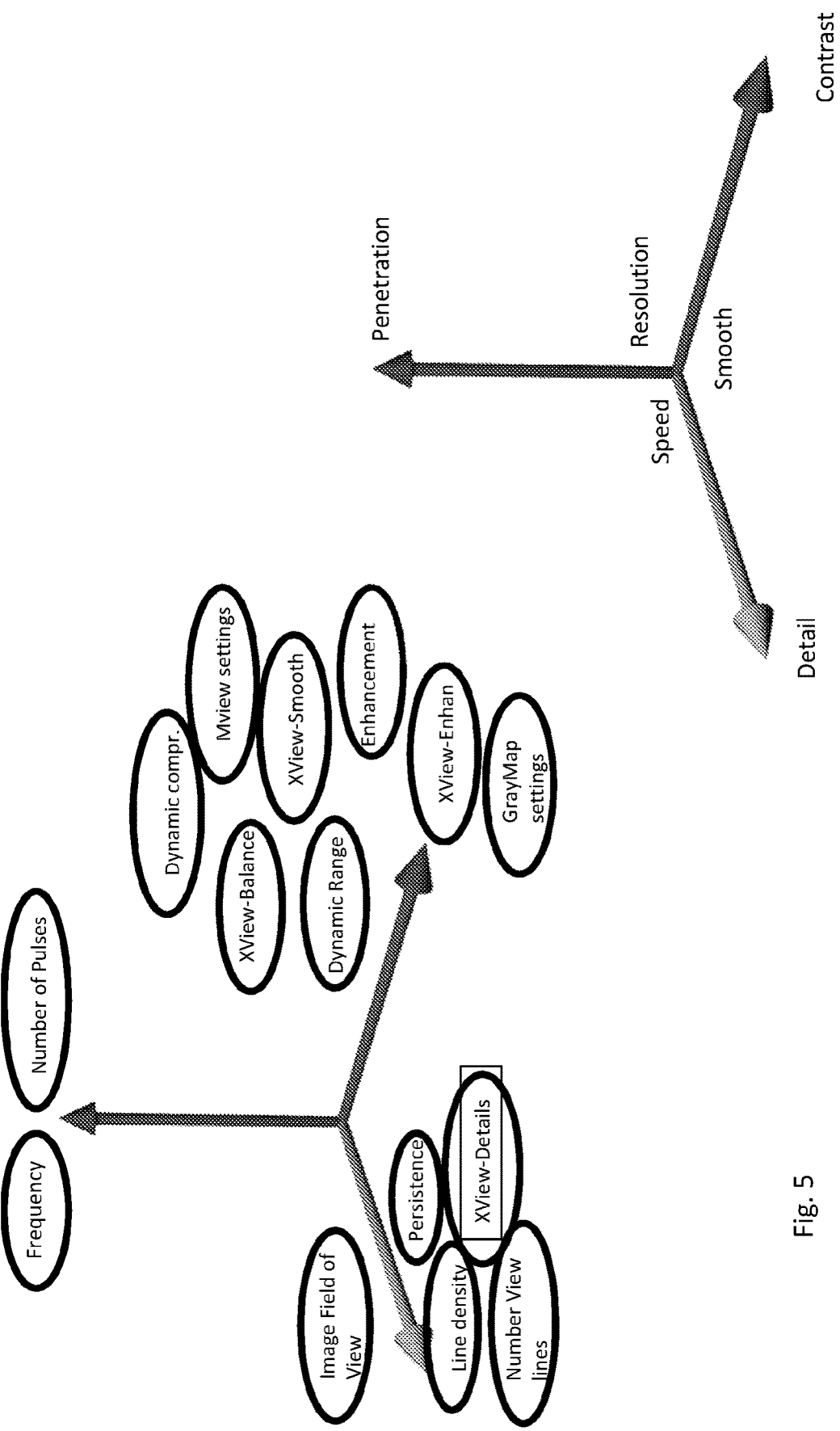
FIG. 5 diagrammatically shows the reduction of the dimension of a multidimensional space of parameters influencing the image appearance when passing from the standard tuning to the current tuning method.

According to a non-limiting specific embodiment of FIGS. 4 and 5, the individuated image appearance features 400 are indicated in the left box 401, 402, 403 as three different combinations of complementary image appearance features:

penetration-resolution
speed-detail
smooth-contrast.

The feature of each couple are antithetic features of the image appearance which are determined by the same combination of standard workflow setting parameters as it is indicated in the left box 410 by the sub groups of standard workflow setting parameters 411, 412, 413. The standard workflow setting parameters of each sub group are the ones having an influence on the image appearance feature of the corresponding couple of image appearance features. According to the specific embodiment of FIG. 4 the specific combination of standard workflow setting parameters 410 related to the three couples of image appearance features are:
the penetration-resolution ratio image appearance feature control parameter is a function of the following standard workflow setting parameters: frequency, number of transmit pulses;
the speed-detail ratio image appearance feature control parameter is a function of the following standard workflow setting parameters: Image field of view, Persistence, Line density, Number of view lines and XView-details;
the smooth-contrast ratio image appearance feature control parameter is a function of the following standard workflow setting parameters: Dymanic compression, dynamic range, enhancement, graymap settings, MView settings, Xview-balance, Xview-Smooth, XView-enhancement.

It has to be appreciated that by passing from the standard tuning interface to the new tuning interface, the number of different parameters to be controlled has reduced from 15 to only 3 parameters. Furthermore the definition of the image appearance features control parameters sets a direct relation between the value of the parameter and the condition of the image appearance relating to the corresponding appearance feature. Differently as per definition, the standard workflow setting parameters are directly related to the physical parameters of the imaging system and process and do not have a direct relation to the image appearance so that anon-skilled person having no deep insight into the physics of the ultrasound system will have difficulties in determining which parameters to change in order to obtain a certain image appearance effect and in many cases there will be the possibility that although the desired image appearance may be more or less obtained this has been achieved by using a combination of settings of the standard workflow setting parameters which is detrimental for the quality of the image or leads to bad images in relation to the information content.

FIG. 5 shows the concept of FIG. 4 in a graphic way. Starting from a multidimensional space of setting parameters, the space of image appearance tuning has reduced to three dimensions, each dimension uniquely related to a combination of complementary image appearance features and corresponding to an image appearance feature control parameter directly related to the image appearance feature in the final image.

The standard workflow setting parameters and the values of the said parameters associated with each value of an image appearance feature control parameter are factory predefined.

Figure 2:
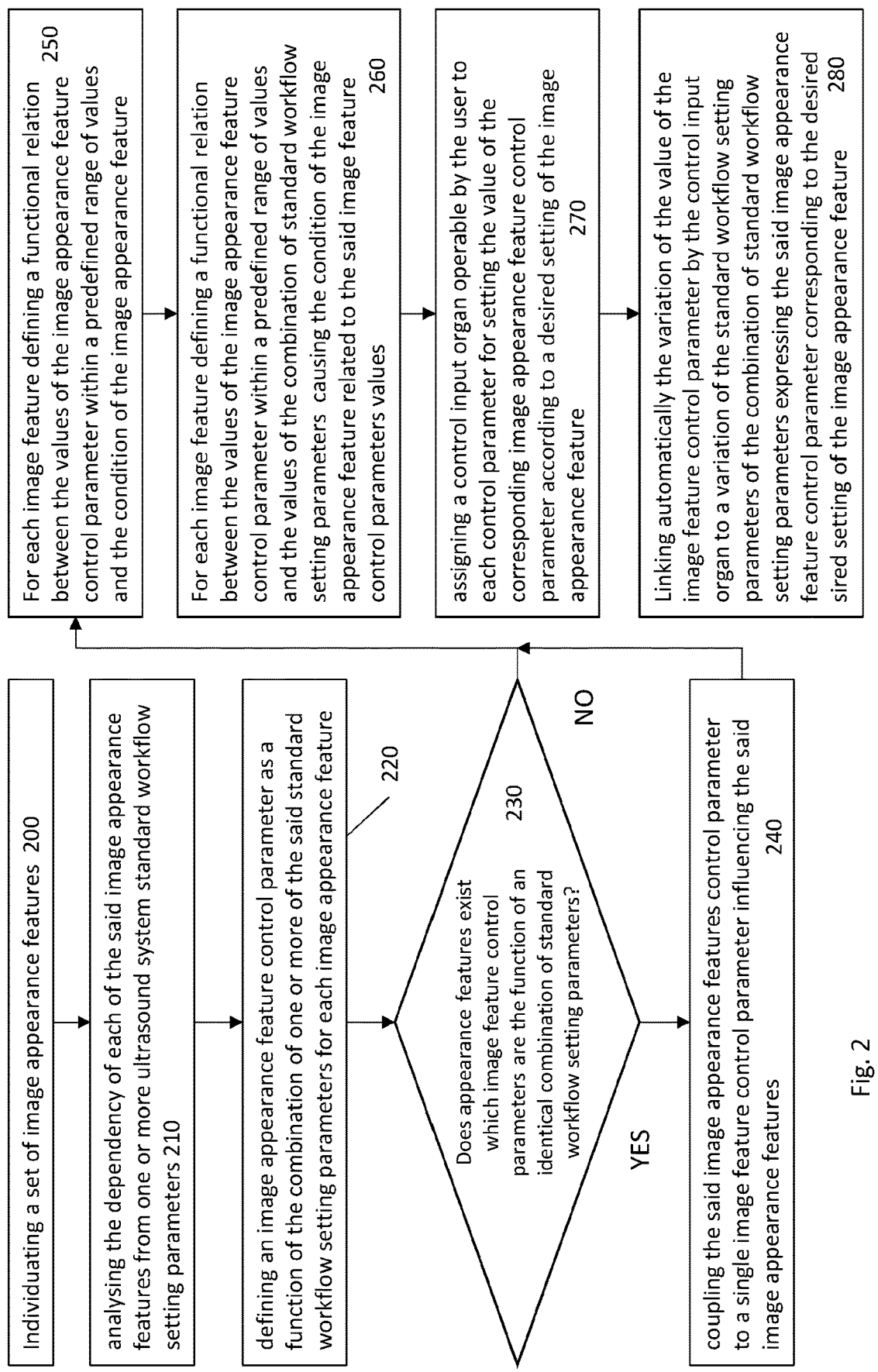
FIG. 2 is a flux diagram showing the steps for generating the image appearance feature control user interface according to embodiments of the present disclosure.

FIG. 2 shows a flux diagram representing the steps of an embodiment of a process for generating the image control user interface according to example embodiments of the present disclosure. At the step 200 an analysis of the user relevant image appearance features is carried out for individuating a set of image appearance features. At step 210 the dependency of each of the said image appearance features from one or more ultrasound system standard workflow setting parameters is determined. Basing on this result an image appearance feature control parameter is defined as a function of the combination of one or more of the said standard workflow setting parameters for each image appearance feature as indicated at step 220. At step 230 the analysis is depended in order to ascertain if there are complementary related image appearance features. One main criterion is the fact to consider if there are different image appearance features whose image appearance feature control parameter is dependent from the same combination of standard workflow setting parameters. In an affirmative case, at step 240 a coupling of these feature is provided by assigning a common image appearance feature control parameter who determines the ration of combination of the two image appearance feature from one extreme condition in which one feature prevails on the other in intermediate conditions in which a combination of both features is provided. After step 240 or if no coupling step is necessary the process is continued by step 250. At this step, for each image appearance feature a functional relation between the values of the image appearance feature control parameter within a predefined range of values and the condition of the image appearance feature is defined. In a following step 260, for each image appearance feature, a functional relation is defined between the values of the image appearance feature control parameter within a predefined range of values and the values of the combination of standard workflow setting parameters causing the condition of the image appearance feature related to the said image appearance feature control parameters values. In order to render the interface operative step 270 provides for assigning a control input organ operable by the user to each control parameter for setting the value of the corresponding image appearance feature control parameter according to a desired setting of the image appearance feature. At step 280, the image appearance feature control parameter is automatically linked to the combination of standard workflow setting parameters, so that the variation of the value of the image appearance feature control parameter by the control input organ automatically determines a variation of the standard workflow setting parameters of the combination of standard workflow setting parameters expressing the said image appearance feature control parameter corresponding to the desired sired setting of the image appearance feature.

Figure 6A:
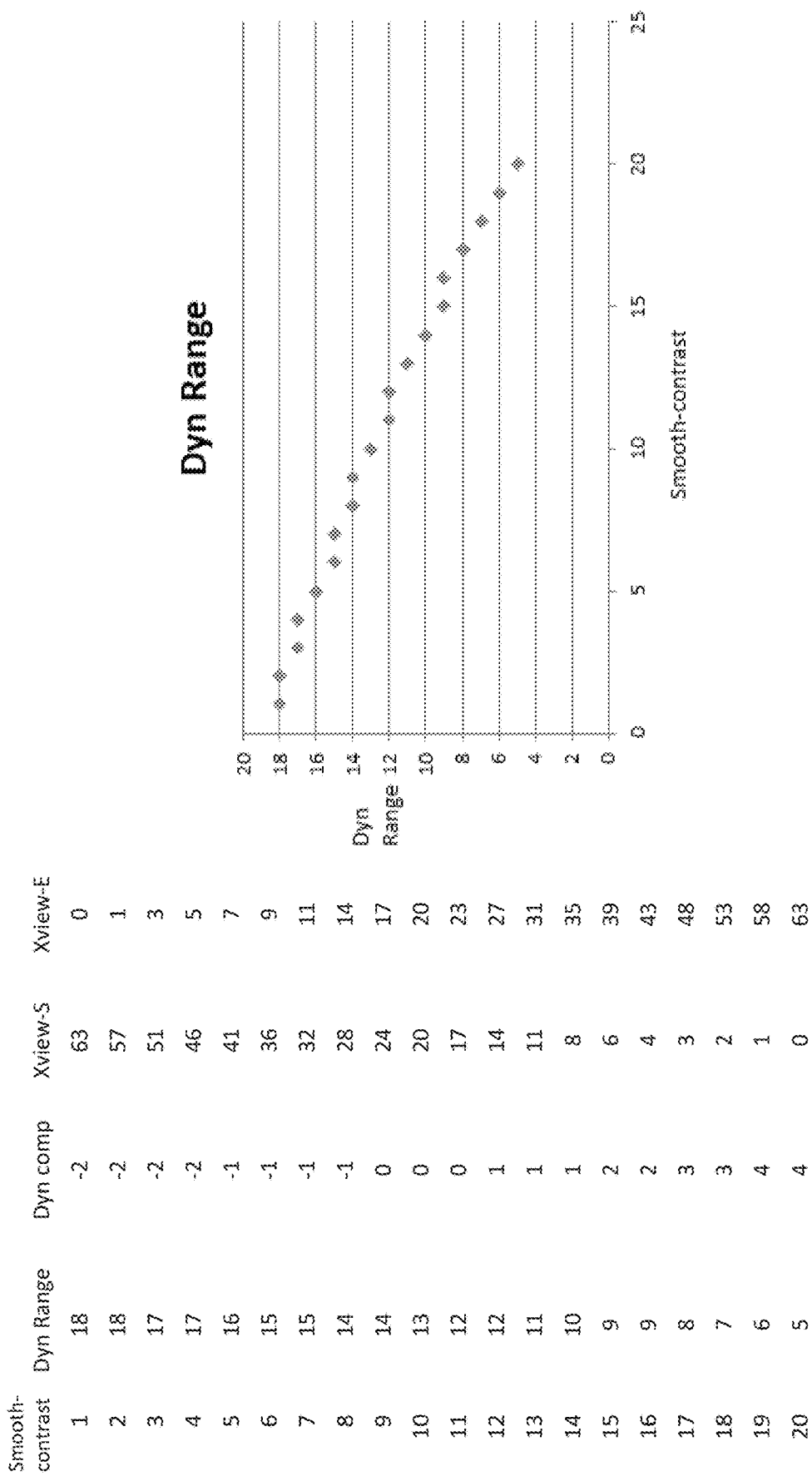
FIGS. 6A, 6B and 6C show the relation between an image appearance feature control parameter and the standard workflow setting parameters whose combination defines the image appearance feature control parameter, respectively according to a first function correlating the values of the image appearance feature control parameter and the values of the corresponding standard workflow setting parameter influencing the appearance of the image appearance feature related to the control parameter, according to a modified value of a standard workflow setting parameter corresponding to a value of the image appearance feature control parameter, and according to a modified new function describing the said relation.
Figure 6B:
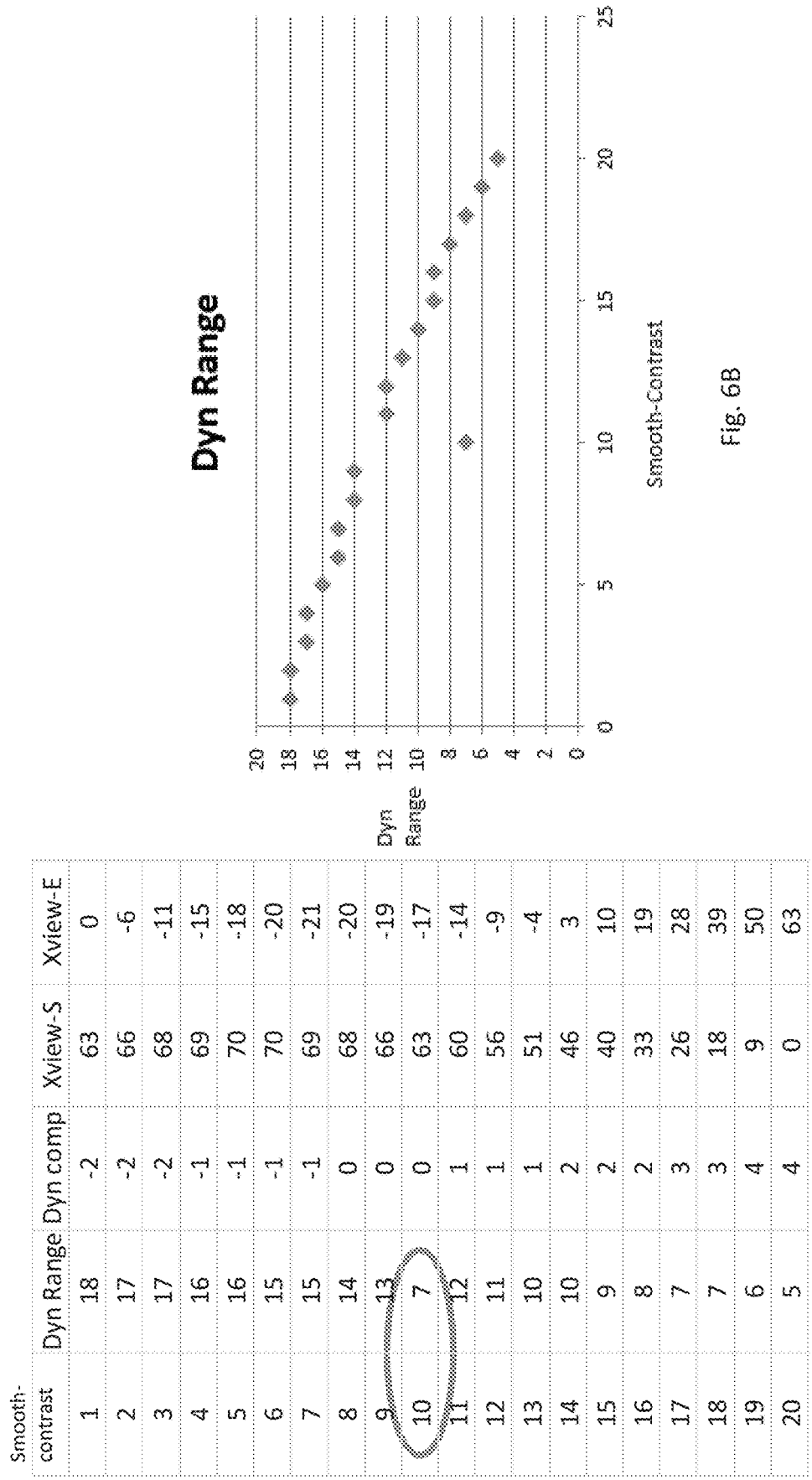
Figure 6C:
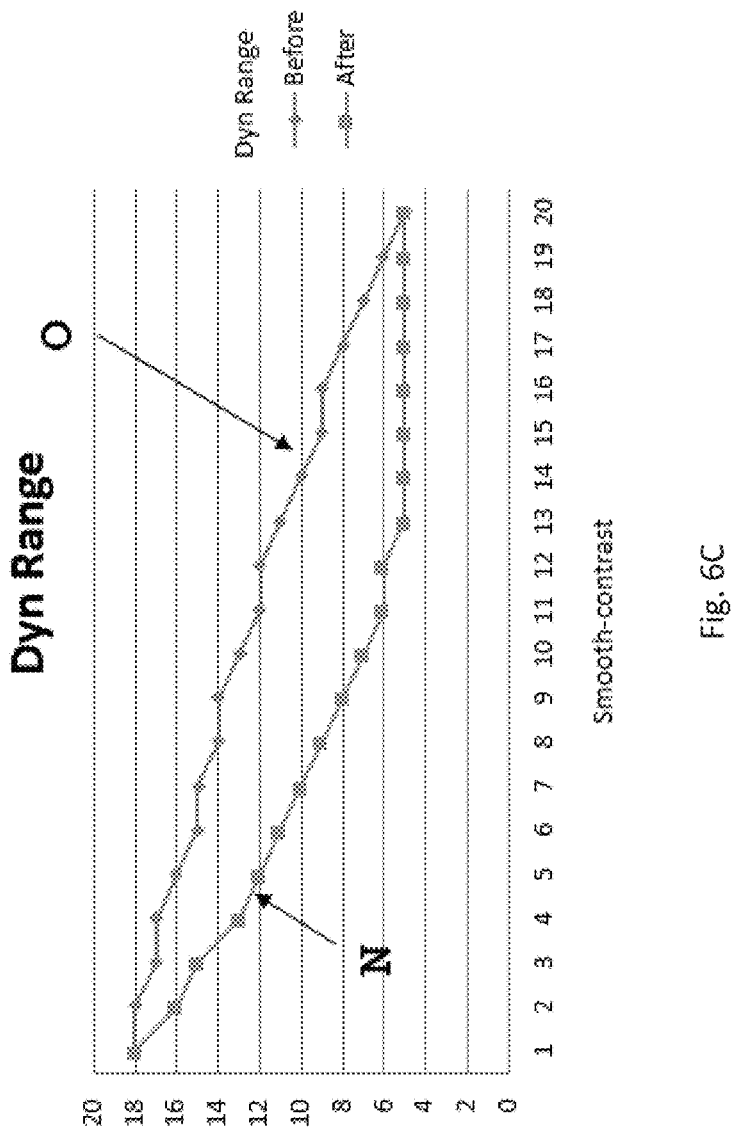
Figure 6C:
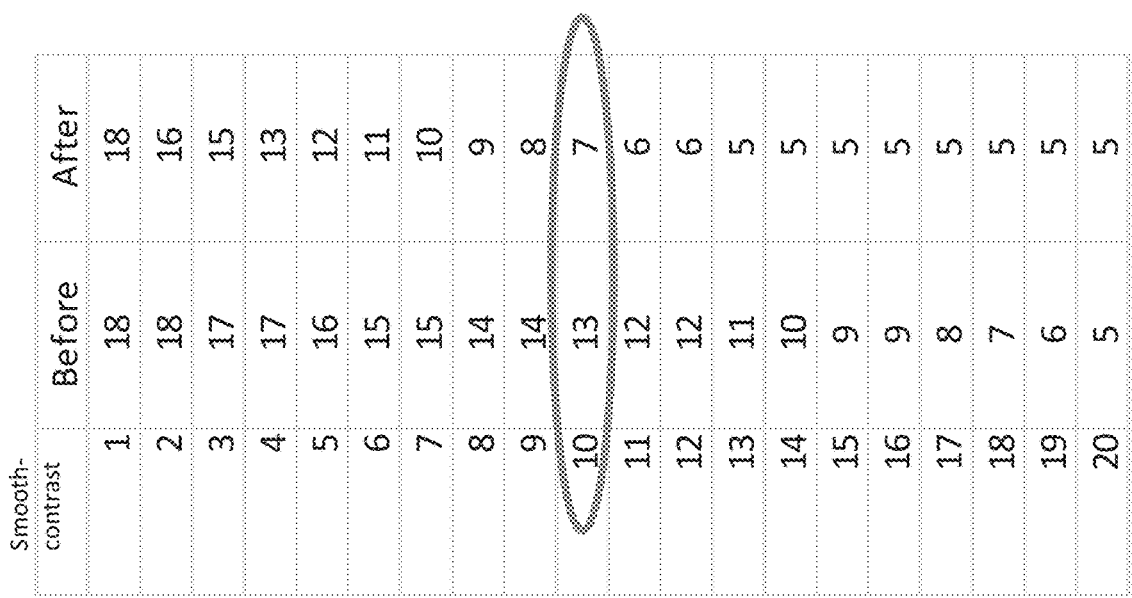
Figure 6D:
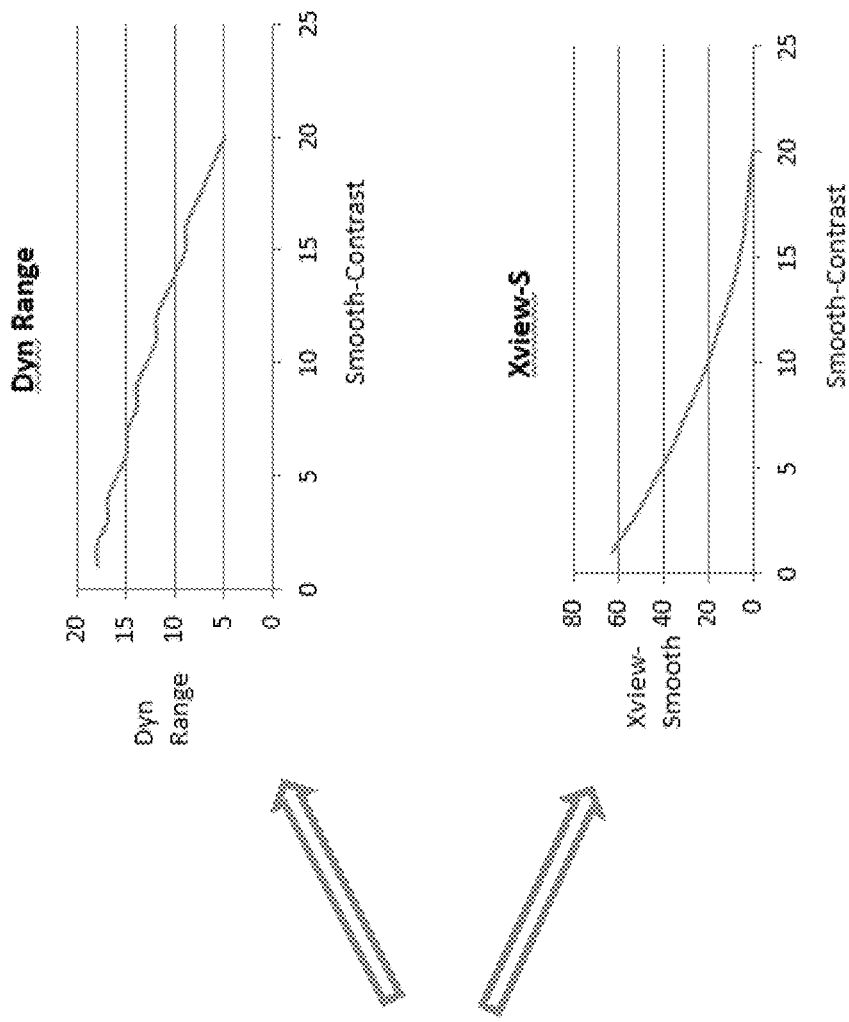
FIG. 6D shows in a similar way as in FIGS. 6A to 6C the functional relation between the image appearance feature control parameter and the standard workflow setting parameter.

The embodiment according to FIG. 6D shows the relation between the image appearance feature control parameter associated with the image appearance feature smooth-contrast and the standard workflow setting parameters which controls the image appearance feature smooth-contrast and which define the image appearance feature control parameter.

On the left side of the FIG. 6D the embodiment of the functional relation between image appearance feature control parameter and each standard workflow setting parameter are in the form of a database or of a look-up table. The first line defines three columns indicating three conditions of the image appearance feature as smooth, default and contrast. Each line of each column is related to a standard workflow setting parameter and gives the corresponding value of it.

In this simplified table the values of the image appearance feature control parameter are summarized by the three conditions smooth, default and contrast corresponding a three different numerical values of the said parameters in a scale of numerical values. In an alternative embodiment the first line could have indicated the numerical values of the image appearance feature control parameter for the three conditions of for more than the three conditions.

The right side of FIG. 6D illustrate a variant embodiment in which the relation between each of the standard workflow setting parameters and the image appearance feature control parameter is defined independently for each standard workflow imaging parameter by a function. The example of FIG. 6D is limited to the two standard workflow setting parameters Dynamic Range and Xview-Smooth. It has to be noted that each function is different.

It has to be noted that according to the above embodiment, when a variation of the value of one image appearance feature control parameter is carried out in order to obtain a variation of the image appearance relatively to the corresponding appearance feature, the values of each of the standard workflow setting parameters of the combination defining the said image appearance feature control parameter are varied independently each one according to the specific function or database describing the relation between the standard workflow setting parameter and the image appearance feature control parameter. This means that the combination of values of the standard workflow setting parameters is determined for each value of the image appearance feature control parameter in such a way that a best setting of the single standard workflow setting parameters compatible with the image appearance feature variation requested is chosen, thereby avoiding combinations which may obtain similar image appearance results but corresponds to non-favourable or detrimental settings of the standard workflow setting parameters in relation to other qualitative features of the image.

The functions may be determined numerically by approximating empirical or experimental data and are factory defined as the database or look up tables and stored in the memory of the ultrasound system.

Figure 3:
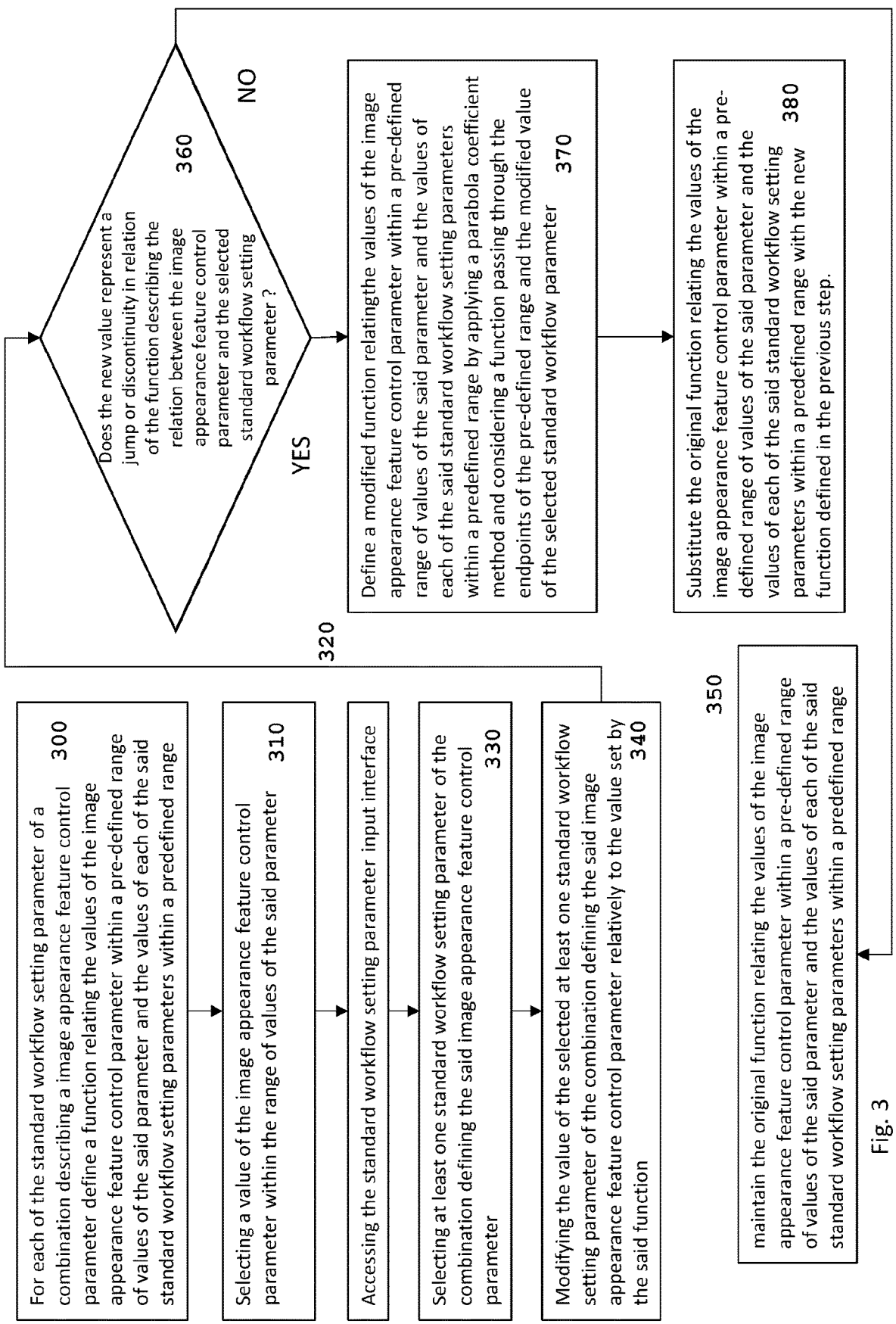
FIG. 3 illustrates a flux diagram showing the steps for generating a new function relating the image appearance feature control parameter to a standard workflow setting parameter when the value of the said standard workflow setting parameter is changed by the user.

FIG. 3 is a flux diagram of an embodiment of the present disclosure according to FIGS. 1A and 1B comprising a user interface for controlling directly the standard workflow setting parameters and a user interface for controlling the image appearance feature control parameter. This two interfaces can be activated in parallel and the user may alternatively operate in controlling one or more of the image appearance feature control parameters and one or more of the standard workflow setting parameter thereby jumping from one image interface to the other.

According to an embodiment operation on the standard workflow setting parameters may be carried out by changing one or more values of the said standard workflow setting parameters which are related to a value set by the database or look up table or by the function defining the relation the relation between the standard workflow setting parameter and the image appearance feature control parameter.

FIG. 3 shows the step of an embodiment of these process. At step 300, for each of the standard workflow setting parameter of a combination describing a image appearance feature control parameter a function is defined relating the values of the image appearance feature control parameter within a pre-defined range of values of the said parameter to the values of each of the said standard workflow setting parameters within a predefined range. Generally this function is in the form of a database or of a lookup table but a function may be numerically determined by approximation of the empirically or experimentally determined data comprising the values of the standard workflow setting parameters related to a value of the image appearance feature control parameter. At step 310 a value for the image appearance feature control parameter within the range of values of the said parameter is selected.

Jumping to the user interface for controlling the standard workflow setting parameters directly 320, at least a standard workflow setting parameter of the combination defining the said image appearance feature control parameter is selected, as shown in 330. At step 340, the value of the selected at least one standard workflow setting parameter of the combination defining the said image appearance feature control parameter is modified relatively to the value set by the said function. The continuity discontinuity of the said modified value in relation to the function relating the values of the said standard workflow setting parameter to the values of the image appearance feature control parameter is analysed at step 360. Discontinuity may be determined if the distance of the modified value in relation to the previous value and to the other values defined by the function overcomes a certain threshold. If this is not the case, step 350 is executed and the original function is maintained by changing the original value with the modified value. If the modified value is considered a discontinuity step 370 is carried out. In this step a modified function relating the values of the image appearance feature control parameter within a pre-defined range of values of the said parameter and the values of each of the said standard workflow setting parameters within a predefined range is calculated. Several alternative algorithms may be applied for calculating this new function. According to an embodiment a parabola coefficient method is applied for calculating the new function. According to an embodiment the said new function is set to pass at the endpoints of the pre-defined range and at the modified value of the selected standard workflow parameter. Once the said new function has been determined which can be either in the form of a database or of a look up table or as a numerically calculated function, step 380. According to the present embodiment, the original function relating the values of the image appearance feature control parameter within a pre-defined range of values of the said parameter and the values of each of the said standard workflow setting parameters within a predefined range is substituted with the new function defined in the previous step 370.

FIGS. 6A to 6C illustrates a specific example of the above generic embodiment of the method. On its left side FIG. 6A shows the functional relation of the values of the image appearance feature control parameter, which in this case is the smooth-contrast ratio parameter, in the form of a look up table. The data are graphically represented in the right side of FIG. 6A. A function could be numerically determined approximating the path defined by the points of the graph. Each value of the image appearance feature control parameter smooth-contrast corresponds to a different combination of values of the standard workflow setting parameters.

FIG. 6B shows the variation of the value of the Dynamic Range standard workflow setting parameter corresponding to the value of the smooth-contrast parameter of 10. The value is changed from 13 (FIG. 6A) to 7 (FIG. 6B). On the right side this situation is represented in the graph. The discontinuity can be at once recognized. The new value of Dyn range falls far away from the rest of the values of the said parameter.

In FIG. 6C this situation is clearly highlighted the table shows the values of the parameter smooth-contrast and the corresponding values of the Dyn range parameter before and after the variation of the value from 13 to 7 corresponding to the value 10 of the smooth-contrast parameter. In the right hand graphical reproduction the function 0 approximating the original relation between the values of the parameter smooth-contrast and Dyn range is shown beside the new function N approximating the new set of values for the parameter Dyn range according to the column after and comprising the modified value from 13 to 7. The new function has modified all the values between the two end points of the graph and the new set value 7 for the Dyn range parameter. This new function has been approximated using the method of the parabola coefficients.

FIG. 3 is a flux diagram representing the steps of FIGS. 6A to 6C.

FIGS. 7A to 7D show different embodiments of the control input organs for setting the image appearance feature control parameters particularly related to the selection of image appearance features of the embodiment of FIG. 4. In a first embodiment of FIG. 7A the input control organs are in the form of cursors or sliders 700. There is provided a separate cursor or slider for each of the selected image appearance feature to which an image appearance feature control parameter is associated.

In the embodiment of FIG. 7B the input control organs 710 are in the form of knobs which can be rotated. In the embodiment of FIG. 7C the input control organ is in the form of a Joystik 720 combining in one organ different control organs for different image appearance feature control parameters. According to the arrows, the forward backward motion of the joystick lever controls the smooth-contrast image appearance feature, the left right motion the speed/details image appearance feature. A further knob may be provided which vary by pressure the frequency of the beams from fundamental to other values.

The above input control organs are in the form of physical objects which are hand operated, but they may be substituted by virtual objects represented by corresponding icons on a screen. This is the case of the GUI shown in FIG. 7D. Here three slider input control organs are shown which despite a different aesthetic aspect are virtual representations of the slider of FIG. 7A. If a normal screen is used the slide setting can be operated by using a trackball or a mouse or similar input devices by clicking on the slider cursor 730 and shifting it by the mouse or trackball motion. In case of a touch-screen interface, the slider cursors 730 may be activated and displaced by finger touch on the screen.

Figure 7D:
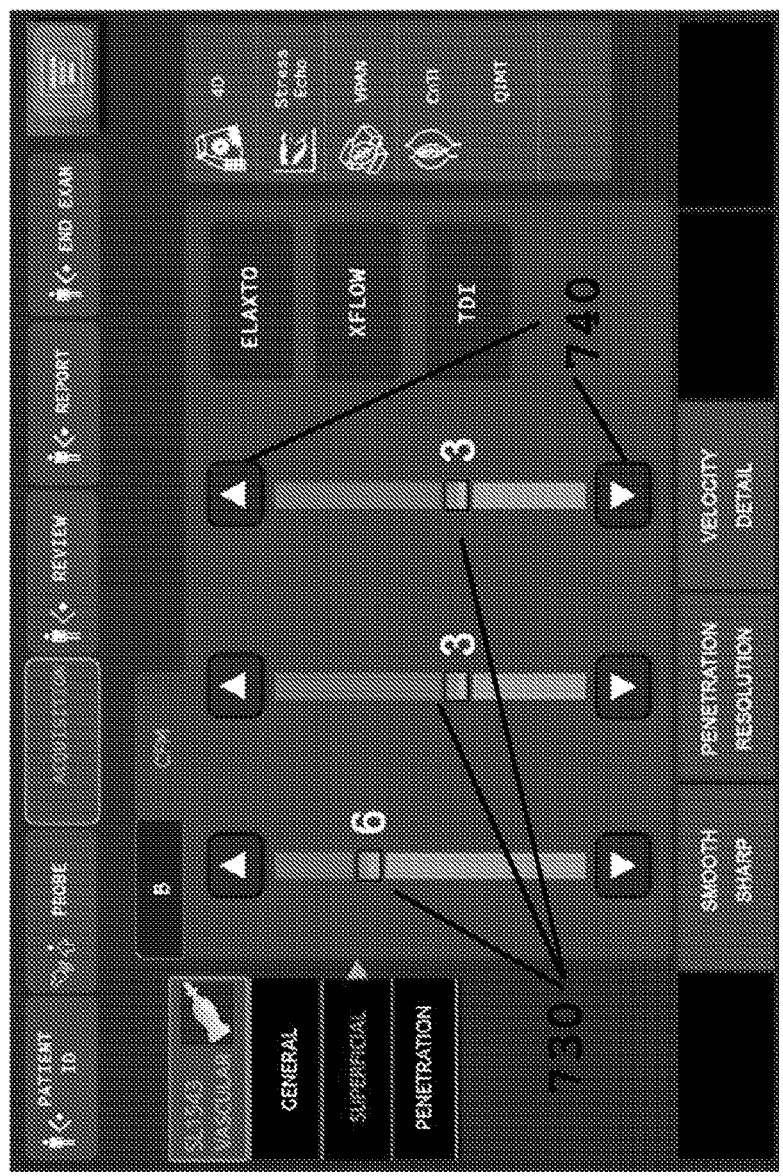

Alternatively, the slider cursor 730 may be displaced by clicking or tipping on the arrows at both ends of each slider which are indicated by 740 in FIG. 7D.

Figure 8:
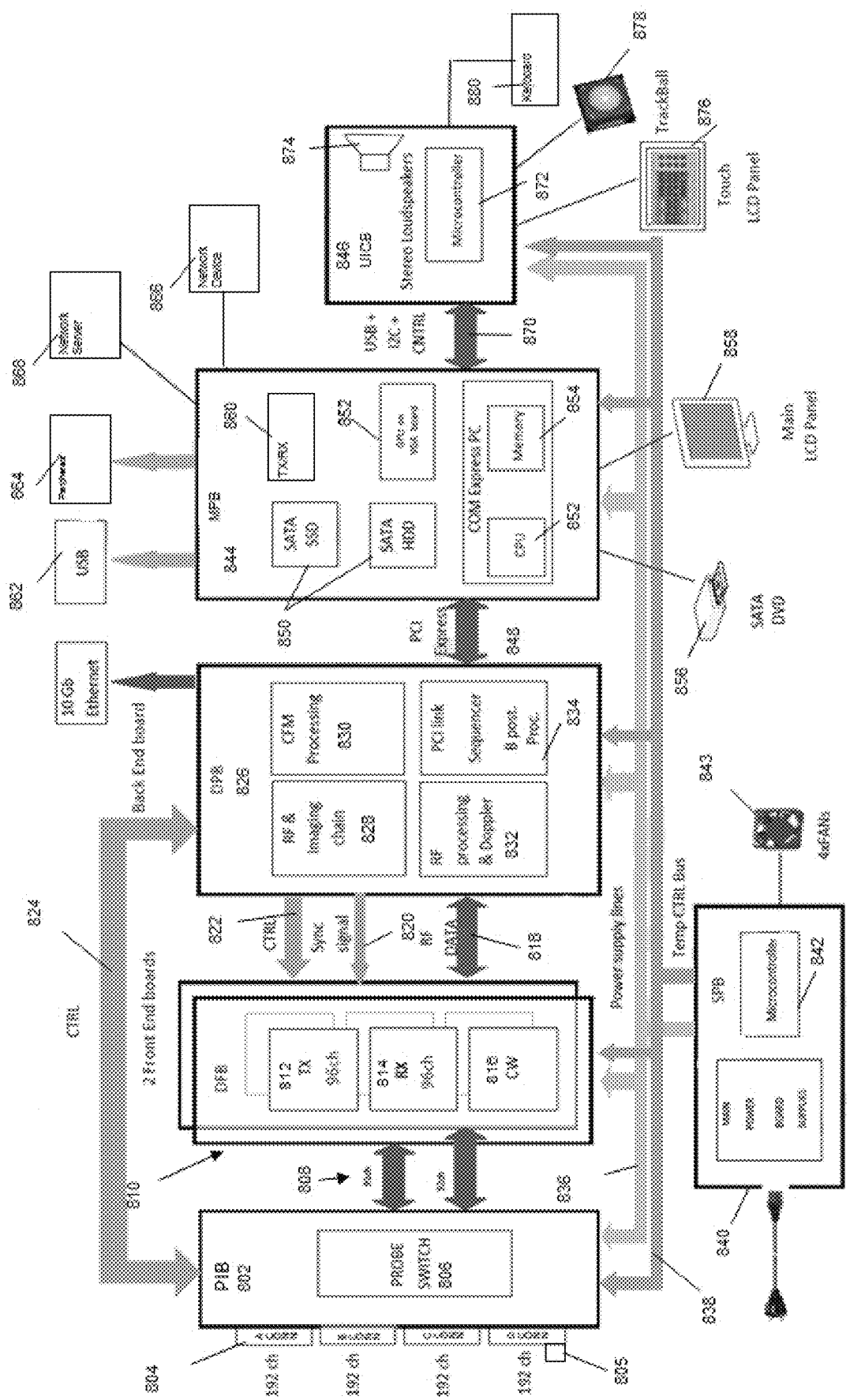
FIG. 8 illustrates a block diagram of an ultrasound system formed in accordance with an alternative embodiment.

FIG. 8 illustrates a block diagram of an ultrasound system formed in accordance with an alternative embodiment. The system of FIG. 8 implements the operations described herein in connection with various embodiments. By way of example, one or more circuits/processors within the system implement the operations of any processes illustrated in connection with the figures and/or described herein. The system includes a probe interconnect board 802 that includes one or more probe connection ports 804. The connection ports 804 may support various numbers of signal channels (e.g., 128, 192, 256, etc.). The connector ports 804 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynaecological, urological and cerebrovascular examination, breast examination and the like.

One or more of the connection ports 804 may support acquisition of 2D image data and/or one or more of the connection ports 804 may support 3D image data. By way of example only, the 3D image data may be acquired through physical movement (e.g., mechanically sweeping or physician movement) of the probe and/or by a probe that electrically or mechanically steers the transducer array.

The probe interconnects board (PIB) 802 includes a switching circuit 806 to select between the connection ports 804. The switching circuit 806 may be manually managed based on user inputs. For example, a user may designate a connection port 804 by selecting a button, switch or other input on the system. Optionally, the user may select a connection port 804 by entering a selection through a user interface on the system.

Optionally, the switching circuit 806 may automatically switch to one of the connection ports 804 in response to detecting a presence of a mating connection of a probe. For example, the switching circuit 806 may receive a "connect" signal indicating that a probe has been connected to a selected one of the connection ports 804. The connect signal may be generated by the probe when power is initially supplied to the probe when coupled to the connection port 804. Additionally, or alternatively, each connection port 804 may include a sensor 805 that detects when a mating connection on a cable of a probe has been interconnected with the corresponding connection port 804. The sensor 805 provides signal to the switching circuit 806, and in response thereto, the switching circuit 806 couples the corresponding connection port 804 to PIB outputs 808. Optionally, the sensor 805 may be constructed as a circuit with contacts provided at the connection ports 804. The circuit remains open when no mating connected is joined to the corresponding connection port 804. The circuit is closed when the mating connector of a probe is joined to the connection port 804.

A control line 824 conveys control signals between the probe interconnection board 802 and a digital processing board 826. A power supply line 836 provides power from a power supply 840 to the various components of the system, including but not limited to, the probe interconnection board (PIB) 802, digital front end boards (DFB) 810, digital processing board (DPB) 826, the master processing board (M PB) 844, and a user interface control board (UI CB) 846. A temporary control bus 838 interconnects, and provides temporary control signals between, the power supply 840 and the boards 802, 810, 826, 844 and 846. The power supply 840 includes a cable to be coupled to an external AC power supply. Optionally, the power supply 840 may include one or more power storage devices (e.g. batteries) that provide power when the AC power supply is interrupted or disconnected. The power supply 840 includes a controller 842 that manages operation of the power supply 840 including operation of the storage devices.

Additionally, or alternatively, the power supply 840 may include alternative power sources, such as solar panels and the like. One or more fans 843 are coupled to the power supply 740 and are managed by the controller 842 to be turned on and off based on operating parameters (e.g. temperature) of the various circuit boards and electronic components within the overall system (e.g. to prevent overheating of the various electronics).

The digital front-end boards 810 providing analog interface to and from probes connected to the probe interconnection board 802. The DFB 810 also provides pulse or control and drive signals, manages analog gains, includes analog to digital converters in connection with each receive channel, provides transmit beamforming management and receive beamforming management and vector composition (associated with focusing during receive operations).

The digital front end boards 810 include transmit driver circuits 812 that generate transmit signals that are passed over corresponding channels to the corresponding transducers in connection with ultrasound transmit firing operations. The transmit driver circuits 812 provide pulse or control for each drive signal and transmit beamforming management to steer firing operations to points of interest within the region of interest. By way of example, a separate transmit driver circuits 812 may be provided in connection with each individual channel, or a common transmit driver circuits 812 may be utilized to drive multiple channels. The transmit driver circuits 812 cooperate to focus transmit beams to one or more select points within the region of interest. The transmit driver circuits 812 may implement single line transmit, encoded firing sequences, multiline transmitter operations, generation of shear wave inducing ultrasound beams as well as other forms of ultrasound transmission techniques.

The digital front end boards 810 include receive beamformer circuits 814 that received echo/receive signals and perform various analog and digital processing thereon, as well as phase shifting, time delaying and other operations in connection with beamforming. The beam former circuits 814 may implement various types of beamforming, such as single-line acquisition, multiline acquisition as well as other ultrasound beamforming techniques.

The digital front end boards 816 include continuous wave Doppler processing circuits 816 configured to perform continuous wave Doppler processing upon received echo signals. Optionally, the continuous wave Doppler circuits 816 may also generate continuous wave Doppler transmit signals.

The digital front-end boards 810 are coupled to the digital processing board 826 through various buses and control lines, such as control lines 822, synchronization lines 820 and one or more data bus 818. The control lines 822 and synchronization lines 820 provide control information and data, as well as synchronization signals, to the transmit drive circuits 812, receive beamforming circuits 814 and continuous wave Doppler circuits 816. The data bus 818 conveys RF ultrasound data from the digital front-end boards 810 to the digital processing board 826. Optionally, the digital front end boards 810 may convert the RF ultrasound data to I,Q data pairs which are then passed to the digital processing board 826.

The digital processing board 826 includes an RF and imaging module 828, a color flow processing module 830, an RF processing and Doppler module 832 and a peripheral component interconnect (PCI) link module 834. The digital processing board 826 performs RF filtering and processing, processing of black and white image information, processing in connection with color flow, Doppler mode processing (e.g. in connection with polls wise and continuous wave Doppler). The digital processing board 826 also provides image filtering (e.g. speckle reduction) and scanner timing control. The digital processing board 826 may include other modules based upon the ultrasound image processing functionality afforded by the system.

The modules 828-834 comprise one or more processors, DSPs, and/or FPGAs, and memory storing program instructions to direct the processors, DSPs, and/or FPGAs to perform various ultrasound image processing operations. The RF and imaging module 828 performs various ultrasound related imaging, such as B mode related image processing of the RF data. The RF processing and Doppler module 832 convert incoming RF data to I,Q data pairs, and performs Doppler related processing on the I, Q data pairs. Optionally, the imaging module 828 may perform B mode related image processing upon I, Q data pairs. The CFM processing module 830 performs color flow related image processing upon the ultrasound RF data and/or the I, Q data pairs. The PCI link 834 manages transfer of ultrasound data, control data and other information, over a PCI express bus 848, between the digital processing board 826 and the master processing board 844.

The master processing board 844 includes memory 850 (e.g. serial advanced technology attachment (SATA) solid-state devices, SATA hard disk drives, etc.), a video graphics array (VGA) board 852 that includes one or more graphic processing unit (GPUs), one or more transceivers 860 one or more CPUs 852 and memory 854. The master processing board (also referred to as a PC board) provides user interface management, scan conversion and cine loop management. The master processing board 844 may be connected to one or more external devices, such as a DVD player 856, and one or more displays 858. The master processing board includes communications interfaces, such as one or more USB ports 862 and one or more ports 864 configured to be coupled to peripheral devices. The master processing board 844 is configured to maintain communication with various types of network devices 866 and various network servers 868, such as over wireless links through the transceiver 860 and/or through a network connection (e.g. via USB connector 862 and/or peripheral connector 864).

The network devices 866 may represent portable or desktop devices, such as smart phones, personal digital assistants, tablet devices, laptop computers, desktop computers, smart watches, ECG monitors, patient monitors, and the like. The master processing board 844 conveys ultrasound images, ultrasound data, patient data and other information and content to the network devices for presentation to the user. The master processing board 844 receives, from the network devices 866, inputs, requests, data entry and the like.

The network server 868 may represent part of a medical network, such as a hospital, a healthcare network, a third-party healthcare service provider, a medical equipment maintenance service, a medical equipment manufacturer, a government healthcare service and the like. The communications link to the network server 868 may be over the Internet, a private intranet, a local area network, a wide-area network, and the like.

The master processing board 844 is connected, via a communications link 870 with a user interface control board 846. The communications link 870 conveys data and information between the user interface and the master processing board 844. The user interface control board 846 includes one or more processors 872, one or more audio/video components 874 (e.g. speakers, a display, etc.). The user interface control board 846 is coupled to one or more user interface input/output devices, such as an LCD touch panel 876, a trackball 878, a keyboard 780 and the like. The processor 872 manages operation of the LCD touch panel 876, as well as collecting user inputs via the touch panel 876, trackball 878 and keyboard 880, where such user inputs are conveyed to the master processing board 844 in connection with implementing embodiments herein.

Figure 9:
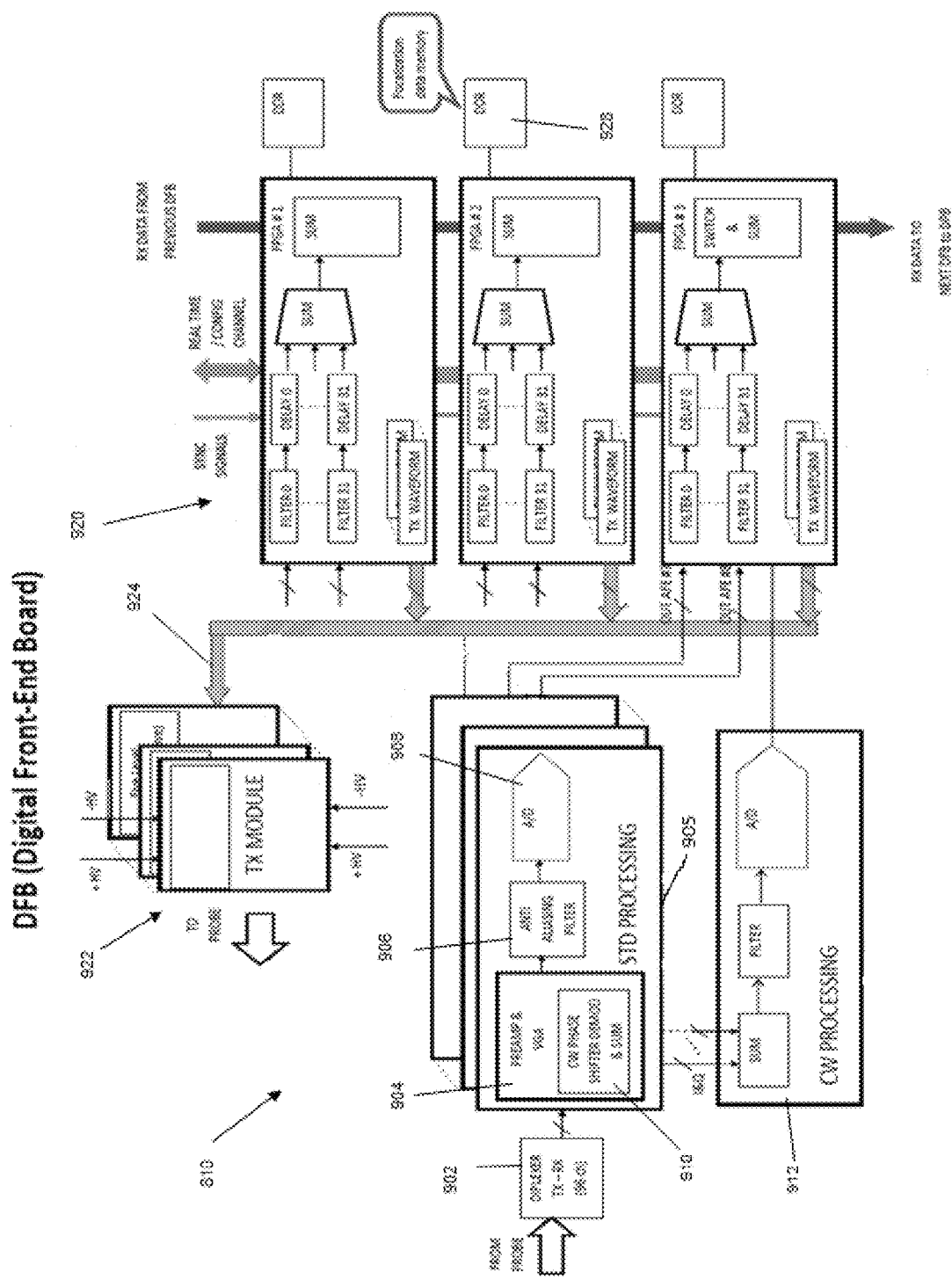
FIG. 9 illustrates a block diagram of a portion of the digital front-end boards of FIG. 8.

FIG. 9 illustrates a block diagram of a portion of the digital front-end boards 810 formed in accordance with embodiments herein. A group of diplexers 902 receive the ultrasound signals for the individual channels over the PIB output 808. The ultrasound signals are passed along a standard processing circuit 905 or to a continuous wave processing circuit 912, based upon the type of probing utilized. When processed by the standard processing circuit 905, a preamplifier and variable gain amplifier 904 process the incoming ultrasound receive signals that are then provided to an anti-aliasing filter 906 which performs anti-aliasing filtering.

According to an embodiment the retrospective transmit beam focusing according to the present disclosure may be applied to the RF data directly acquired by the system or to transformed data according to different transformations as for example as a phase/quadrature (I/Q) transformation, or similar.

In the embodiment of FIG. 9 an example of the said transformation of the RF data is disclosed According to this example, the output of the filter 906 is provided to an A/D converter 908 that digitizes the incoming analog ultrasound receive signals. When a continuous wave (CW) probe is utilized, the signals therefrom are provided to a continuous wave phase shifter, demodulator and summer 910 which converts the analog RF receive signals to I,Q data pairs. The CW I,Q data pairs are summed, filtered and digitized by a continuous wave processing circuit 912. Outputs from the standard or continuous wave processing circuits 905, 912 are then passed to beam forming circuits 920 which utilize one or more FPGAs to perform filtering, delaying and summing the incoming digitized receive signals before passing the RF data to the digital processing board 826 (FIG. 8). The FPGAs receive focalization data from memories 928. The focalization data is utilized to manage the filters, delays and summing operations performed by the FPGAs in connection with beamforming. The beamformed RF or I/Q data is passed between the beamforming circuits 920 and ultimately to the digital processing board 826.

The digital front-end boards 810 also include transmit modules 922 that provide transmit drive signals to corresponding transducers of the ultrasound probe. The beamforming circuits 920 include memory that stores transmit waveforms. The transmit modules 922 receive transmit waveforms over line 924 from the beamforming circuits 920.

Figure 10:
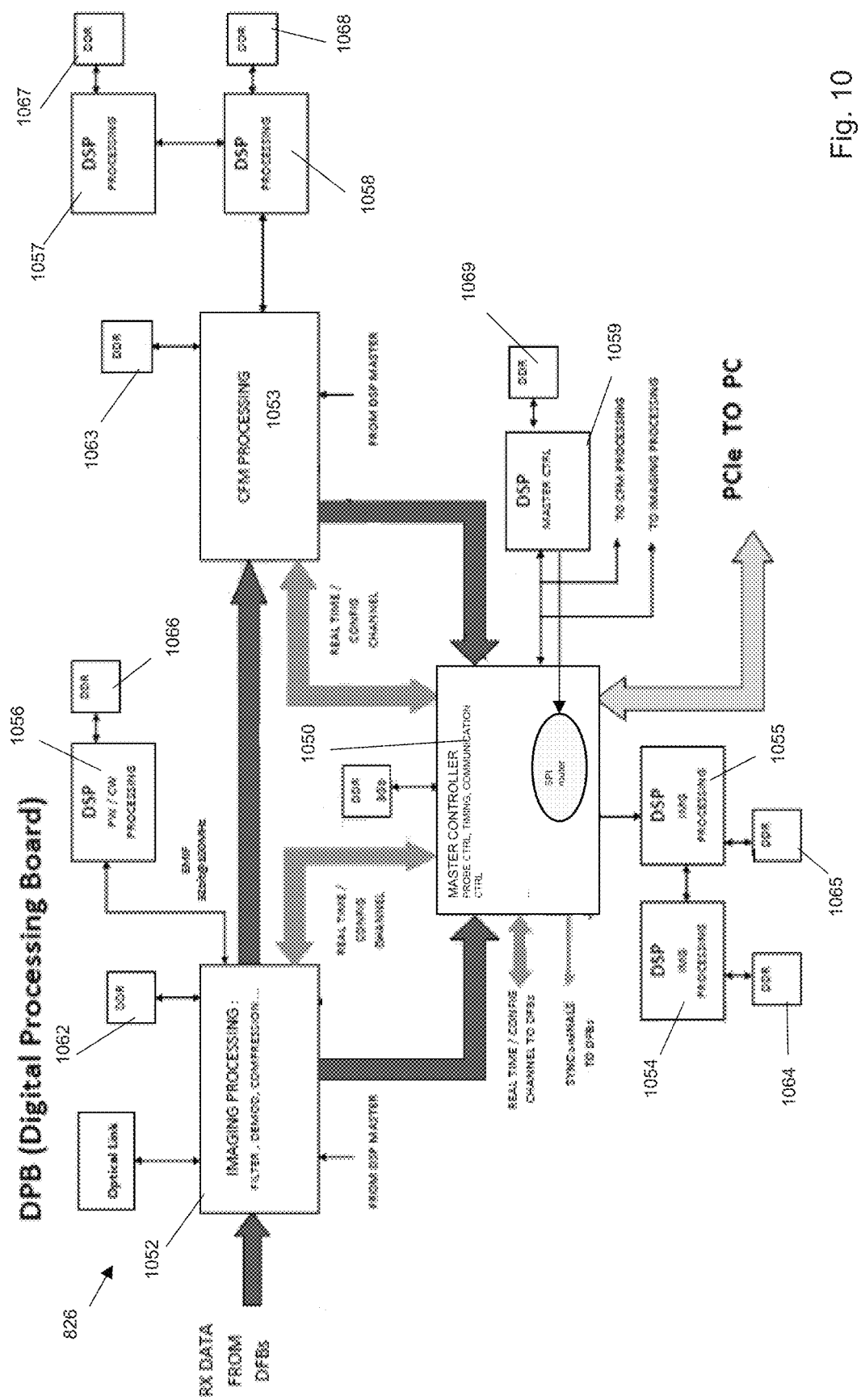
FIG. 10 illustrates a block diagram of the digital processing board of FIG. 8.

FIG. 10 illustrates a block diagram of the digital processing board 826 implemented in accordance with embodiments herein. The digital processing board 826 includes various processors 1052-1059 to perform different operations under the control of program instructions saved within corresponding memories see 1062-1069. A master controller 1050 manages operation of the digital processing board 826 and the processors 1052-1059. By way of example, one or more processors as the 1052 may perform filtering, the modulation, compression and other operations, while another processor 1053 performs color flow processing. The master controller provides probe control signals, timing control signals, communications control and the like. The master controller 1050 provides real-time configuration information and synchronization signals in connection with each channel to the digital front-end board 810.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally, or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, File Transfer Protocol (FTC) servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, hypertext pre-processor (PHP), Perl, Python or tool command language (TCL), as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for controlling an image appearance in ultrasound system, the said method comprising the steps of:
providing a set of image appearance feature control parameters, each one of which is related to an image appearance feature according to a pre-defined relation between a value scale of the said image appearance feature control parameter and an image appearance related to a certain condition of the corresponding image appearance feature;
generating a function between the value of each image appearance feature control parameter and the value of the standard workflow setting parameters of a combination of standard workflow setting parameters influencing the said image appearance feature;
visualizing of the image with the requested image appearance feature;
providing control organs for varying manually by a user one or more of the image appearance features of a displayed image by varying through the said control organs the values of said one or more image appearance feature control parameters; and
varying, automatically without the user, the function used to calculate the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance feature control parameter.

2. A method according to claim 1 in which each image appearance feature control parameter is expressed as a function of a combination of one or more of the standard workflow setting parameters which have an influence on the image appearance feature associated with the said image appearance feature control parameter.

3. A method according to claim 1 in which the said functional relation of the image appearance feature control parameter with a combination of standard workflow setting parameters is factory defined.

4. A method according to claim 1 in which the said factory defined functional relation of the image appearance feature control parameter with a combination of standard workflow setting parameters may be modified by the user.

5. A method according to claim 1 in which the value of each image appearance feature control parameter is associated with a scale or a field of values ranging from a minimum value to a maximum value, the minimum value and the maximum values corresponding to a certain extreme condition of the image appearance feature related to the image appearance feature control parameter a function being defined relating the values of the image appearance feature control parameter to the conditions of appearance of the corresponding image appearance feature.

6. A method according to claim 1 in which each standard workflow setting parameter of the combination of standard workflow setting parameters defining the image appearance feature control parameter is related to the image appearance feature control parameter by a function which may be different from the one of the other standard workflow setting parameters of the combination.

7. A method according to claim 1 in which the factory definition steps of the method comprise the following steps:
 defining a set of independent image appearance features and assigning to each image appearance feature a related image appearance feature control parameter;
 defining the image appearance feature control parameter of each image appearance feature as a function of a combination of one or more ultrasound system standard workflow setting parameters related to the physics of the imaging process and which influence the corresponding image appearance feature;
 for each image appearance feature, generating a correlation between the variation of the image appearance relatively to the image appearance feature and the variation of the value of the corresponding image appearance feature control parameter;
 for each image appearance feature, generating a correlation between the values of the image appearance feature control parameter and the values of the said standard workflow setting parameters of the combination of the said standard workflow setting parameters empirically or experimentally or numerically
 defining for each standard workflow setting parameter a function relating the values of the said image appearance feature control parameter to the values of the standard workflow setting parameter or
 a database or a look-up table consisting in an array of the values of the corresponding image appearance feature control parameter and the values of each of the standard workflow setting parameters defining the image appearance feature associated with a value of the image feature control parameter which values are empirically or experimentally determined;
 the said function being used or the said database or the said look-up table being addressable and readable for:
 relating the value of each image appearance feature control parameter to the value of the standard workflow setting parameters of a combination of standard workflow setting parameters influencing the said image feature;
 varying, automatically without the user, the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance feature control parameter.

8. A method according to claim 1 in which the said function relating the values of the said image appearance feature control parameter to the values of the standard workflow setting parameter of the combination of standard workflow setting parameter describing the image appearance feature control parameter is determined numerically by calculating the best fit curve of empirically or experimentally measured relation between different image appearance conditions of an image appearance feature, the corresponding value of the image appearance feature control parameter and the corresponding values of the standard workflow setting parameters of the combination of standard workflow setting parameter describing the image appearance feature control parameter.

9. A method according to claim 1 wherein image appearance feature control parameters are set for at least two of the following image appearance features:
 Penetration-resolution ratio;
 speed-detail ratio; and
 smooth-contrast ratio.

10. A method according to claim 9, in which
 the penetration-resolution ratio image appearance feature control parameter is a function of at least one of the following standard workflow setting parameters: frequency, number of transmit pulses;
 the speed-detail ratio image appearance feature control parameter is a function of at least one of the following standard workflow setting parameters: Image field of view, Persistence, Line density, Number of view lines and XView-details;
 the smooth-contrast ratio image appearance feature control parameter is a function of at least one of the following standard workflow setting parameters: Dynamic compression, dynamic range, enhancement, graymap settings, MView settings, Xview-balance, Xview-Smooth, XView-enhancement.

11. A method according to claim 1 providing a control input organ operable by the user for each control parameter, for setting the value of the corresponding image appearance feature control parameter according to a desired setting of the image appearance feature, which control input organ has two extreme positions each one being related to one of two image appearance feature defined by the same combination of standard workflow setting parameters and which image appearance feature are complementary one to the other so that at one end position a first of the said two image appearance feature prevails and at the opposite end position a second of the said two image appearance feature prevails and in the intermediate positions of the control input organ a combination of the two image appearance features is generated, which combination has different ratio of the said image appearance features as a function of the position of the control input organ between the two extreme end positions.

12. A method according to claim 1 further comprising the steps of
 modifying the value of at least one of the standard workflow setting parameters of the combination of standard workflow setting parameters defining an image appearance feature control parameter corresponding to a certain value of the said image appearance feature control parameter with respect to a factory defined value;

determining a continuity/discontinuity threshold for the modified value relative to the function describing the relation between the image appearance feature control parameter and the said standard workflow setting parameter, the continuity/discontinuity threshold corresponding to a selected distance between the modified value and a previous value defined by the said function;

determining by comparing with the said continuity/discontinuity threshold if the modified values exceed the selected distance to determine a discontinuity in the function describing the relation between the image appearance feature control parameter and the said standard workflow setting parameter, and defining a new function different from the said function describing the relation between the image appearance feature control parameter and the said standard workflow setting parameter by an approximation curve passing through the end points of the value range for the said standard workflow setting parameter and through the said modified value of the said standard workflow setting parameter;

substituting the previous function with the new function and using the new function for determining the values of the standard workflow setting parameter as a function of the image appearance feature control parameter.

13. A method according to claim 12 in which the definition of the new function is an approximation determined using a parabola coefficient method.

14. Image appearance feature control user interface comprising:

a control input organ operable by the user and univocally associated with at least one image appearance feature, for manually setting the value of the corresponding image appearance feature control parameter according to a desired setting of the corresponding image appearance feature to vary manually one or more of the image appearance features of a displayed image;

the said control input organ having two extreme positions each one being related to at least one of two extreme conditions of the said image appearance feature while in the intermediate positions of the control input organ between the said two extreme positions continuously or discretely varying image appearance is set relating to the said image appearance feature as a function of the variation of the value of the corresponding image appearance feature control parameter caused by varying the position of the said control input organ between the said two extreme positions;

the image appearance feature control parameter being a function of a combination of standard workflow setting parameters of the ultrasound scanner which influence the corresponding image appearance feature such that, by manually operating the control input organ in order to vary the image appearance feature determined by a certain value of the image appearance feature control parameter, the corresponding values of the combination of the standard workflow setting parameters determining the requested condition of the image appearance feature are automatically set without the user by the function describing the relation between the image appearance feature control parameter and the said standard workflow setting parameters, and the said function is varied, automatically without the user, to calculate the value of the one or more of the said standard workflow setting parameters of the combination of standard workflow setting parameters influencing an image appearance feature as a function of a variation of the value of the corresponding image appearance feature control parameters for obtaining the image appearance feature variation requested via the control input organ.

15. An image appearance feature control interface according to claim 14 in which the same control input organ is associated for controlling two or more image complementary appearance features whose image appearance feature control parameters are the function of an identical combination of standard workflow setting parameter of the ultrasound system and coupling the said image appearance feature control parameters to a single image feature control parameter influencing the said image appearance features;

defining a correlation function between the corresponding image appearance feature control parameter and the control input organ position between the two extreme positions such that one end position of the control input organ a first of the said two image appearance features prevails, and at the opposite end position a second of the said two image appearance features prevails, and in the intermediate positions of the control input organ a combination of the two image appearance features is generated, which combination has different ratio of the said image appearance features as a function of the position of the control input organ between the two extreme end positions.

16. An image appearance feature control user interface according to claim 14 comprising with a control input organ for one or more of the following couple of complementary image appearance features:

Penetration-resolution ratio speed-detail ratio;

smooth-contrast ratio.

17. An image appearance feature control user interface according to claim 14 in which the control input organs are chosen form the following group:

electronically, electrostatically or mechanically hand operable physical control organs such as cursors or knobs or the like, or virtual, hand, gesture or voice operable organs or combination thereof, or graphically represented organs on a screen or on a touchscreen interface.

18. An image appearance feature control user interface according to claim 17, comprising a processing unit and a touch screen display controlled by the said processing unit, the processing unit executing a software configured for printing on screen the icons representing the control organs and for animating the said control organs to change their aspect by operating them through the touch screen interface, thereby generating input signals for setting values for the image appearance feature control parameter associated with the control organ.

19. An image appearance feature control user interface according to claim 14 comprising A processor configured to carry out the following tasks computing a function describing the relation of the values of the corresponding image appearance feature control parameter and the values of each of the standard workflow setting parameters defining the image appearance feature associated with a value of the image feature control parameter which function is numerically determined by approximating empirically or experimentally determined values or determining the values of each of the standard workflow setting parameters defining the image appearance feature associated with a value of the image appearance feature control parameter by addressing a database or a look-up table saved in a memory of the processor and comprising an array of the values of the corresponding image appearance feature control parameter and the values of each of the standard workflow setting parameters defining the image appearance feature associated with a value of the image feature control parameter which values are empirically or experimentally determined, for determining the value of each image appearance feature control parameter to the value of the standard workflow setting parameters of a combination of standard workflow setting parameters influencing the said image feature;

varying, automatically without the user, the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance control parameter;

visualizing of the image with the requested image appearance feature setting.

20. An image appearance feature control user interface according to claim 14, characterized in that it comprises also input control organs of the standard workflow setting parameters for modifying the value of at least one of the standard workflow setting parameters of the combination of standard workflow setting parameters defining an image appearance feature control parameter corresponding to a certain value of the said image appearance feature control parameter with respect to a factory defined value;

And a processor configured for storing a continuity/discontinuity threshold for the modified value relatively to the function describing the relation between the image appearance feature control parameter and the said standard workflow setting parameter and determining by comparing with the said continuity/discontinuity threshold if the modified values determine a discontinuity in the function describing the relation between the image appearance feature control parameter and the said standard workflow setting parameter, and for numerically computing a new function describing the relation between the image appearance feature control parameter and the said standard workflow setting parameter by an approximation curve passing through the end points of the value range for the said standard workflow setting parameter and through the said modified value of the said standard workflow setting parameter;

the processor further substitutes the previous function with the new function and uses the new function for determining the values of the standard workflow setting parameter as a function of the image appearance feature control parameter.

21. An image appearance feature control user interface according to claim 14 characterized in that for the definition of a new function an approximation by a parabola coefficient method is carried out by the processor.

22. An ultrasound system comprising an image appearance feature control interface according to claim 14, which ultrasound imaging system comprises:

an ultrasound probe including an array of transducer elements transforming electric input signals into acoustic transmit signals and transforming acoustic echo signals into electric receive signals;

a transmit beamformer generating the driving input signals for the transducer elements according to a transmit scheme for driving the transducer array to transmit a plurality of transmit beams from an array transducer;

a receive beamformer including a receive signals processing unit configured to process the echo signals received in response to the transmit beams to produce a plurality of receive lines of echo signals;

a signal processing unit processing the echo signals in order to extract image data from the said echo signals an image generation unit producing an image using the said image data;

an image display and an image user input interface for visualizing data images and messages from the ultrasound system to the user and for inputting control settings or selection of operative conditions and or imaging modes or other input data by the user to the ultrasound system, the said image user interface comprising further:

a control input organ operable by the user univocally associated with at least one image appearance feature of the image printed on the image display, for setting the value of the corresponding image appearance feature control parameter according to a desired setting of the corresponding image appearance feature;

the said control input organ having two extreme positions each one being related to at least one of two extreme conditions of the said image appearance feature while in the intermediate positions of the control input organ between the said two extreme positions continuously or discretely varying image appearance is set relating to the said image appearance feature as a function of the variation of the value of the corresponding image appearance feature control parameter caused by varying the position of the said control input organ between the said two extreme positions;

the image appearance feature control parameter being a function of a combination of standard workflow setting parameters of the ultrasound scanner which influence the corresponding image appearance feature such that by operating the control input organ in order to vary the image appearance feature determined by a certain value of the image appearance control parameter the corresponding values of the combination of the standard workflow setting parameters determining the requested image appearance feature are automatically set without the user.

23. An ultrasound system according to claim 22, characterized in that it comprises electronically, electrostatically or mechanically hand operable physical control organs such as cursors or knobs or the like, or the control input organs are virtual, hand, gesture or voice operable organs or graphically represented organs on a screen or on a touch screen interface.

24. An ultrasound system according to claim 22, characterized in that it comprises A processor to which the user interface is connected, the processor being configured to alternatively computing a function describing the relation of the values of the corresponding image appearance feature control parameter and the values of each of the standard workflow setting parameters defining the image appearance feature associated with a value of the image appearance feature control parameter which function is numerically determined by approximating empirically or experimentally determined values or determining the values of each of the standard workflow setting parameters defining the image appearance feature associated with a value of the image feature control parameter by addressing a database or a look-up table saved in a memory of the processor and comprising an array of the values of the corresponding image appearance feature control parameter and the values of each of the standard workflow setting parameters defining the image appearance feature associated with a value of the image appearance feature control parameter which values are empirically or experimentally determined, for determining the value of each image appearance feature control parameter related to the value of the standard workflow setting parameters of a combination of standard workflow setting parameters influencing the said image appearance feature;

varying, automatically without the user, the value of the one or more of the said standard workflow setting parameters of the combination of standard workflow setting parameters influencing an image appearance feature as a function of a variation of the value of the corresponding image appearance feature control parameters for obtaining the image appearance feature variation requested by the variation of the said image appearance control parameter;

visualizing of the image with the requested image appearance feature setting.

25. An ultrasound system according to claim 22 characterized in that it comprises an image control user interface for controlling image appearance features in ultrasound systems having additionally input control organs of the standard workflow setting parameters, the said input control organs configured for modifying the value of at least one of the standard workflow setting parameters of the combination of standard workflow setting parameters defining an image appearance feature control parameter corresponding to a certain value of the said image appearance feature control parameter with respect to a factory defined value;

And a processor communicating with the input control organ and configured for reading the modified value of the standard workflow setting parameter;

storing a continuity/discontinuity threshold for the modified value relative to the said function describing the relation between the image appearance feature control parameter and the said standard workflow setting parameter, the continuity/discontinuity threshold corresponding to a selected distance between the modified value and a previous value defined by the said function, and determining by comparing with the said continuity/discontinuity threshold if the modified values exceed the selected distance to determine a discontinuity in the function describing the relation between the image appearance feature control parameter and the said standard workflow setting parameter, and executing a software for numerically computing a new function different from the said function describing the relation between the image appearance feature control parameter and the said standard workflow setting parameter by an approximation curve passing through the end points of the value range for the said standard workflow setting parameter and through the said modified value of the said standard workflow setting parameter;

the processor further substitutes the previous the said function with the new function, stores the new function in a memory and uses the new function for determining the values of the standard workflow setting parameter as a function of the image appearance feature control parameter.

26. A method for generating an image appearance control end user interface in ultrasound systems comprising the following steps:

defining a set of independent image appearance features, which may be as non limiting example one or more of the following: contrast-smooth, penetration-resolution, speed-detail;

using control organs provided for manually varying one or more of the image appearance features of a displayed image, manually varying through the said control organs the values of said one or more appearance feature control parameters;

analysing the dependency of each of the said image appearance features from one or more ultrasound system standard workflow setting parameters related to the physics of the imaging process, which may be as non-limiting example one or more of the following: Persistence, Image Field of view, Enhancement, Xview-Smooth, Xview-Enhancement, Mview settings, Number of view lines, Xview Details, Dynamic Range, XView-Balance, Frequency Line density, Gray Map settings, Dynamic compression, fundamental Mode, Tei Mode;

for each image appearance feature defining its image appearance feature control parameter as a function of the combination of one or more of the said standard workflow setting parameters resulting from the dependency analysis of the previous step;

for each image appearance feature, generating a correlation between the variation of the image appearance relatively to the image appearance feature and the variation of the value of the corresponding image appearance feature control parameter inputted manually using the said control organs;

for each image appearance feature, automatically generating a correlation between the values of the image appearance feature control parameter and the values of the said standard workflow setting parameters of the combination of the said standard workflow setting parameters defining the said image appearance feature control parameter by the function describing the relation between the image appearance feature control parameter and the said standard workflow setting parameters, the said function being varied, automatically without the user, to calculate the value of the one or more of the said standard workflow setting parameters of the combination of standard workflow setting parameters influencing an image appearance feature as a function of a variation of the value of the corresponding image appearance feature control parameters for obtaining the image appearance feature variation requested via the control organs.

27. A method according to claim 26 comprising the further step of determining image appearance features which image feature control parameters are the function of an identical combination of standard workflow setting parameter of the ultrasound system and coupling the said image appearance features control parameter to a single image feature control parameter influencing the said image appearance features.

28. A method according to claim 26 comprising the further step of assigning a control input organ operable by the user for each control parameter for setting the value of the corresponding image appearance feature control parameter according to a desired setting of the image appearance feature, which control input organ has two extreme positions each one being related to one of two image appearance features defined by the same combination of standard workflow setting parameters and which image appearance features are complementary with each other so that at one end position a first of the said two image appearance features prevails, and at the opposite end position a second of the said two image appearance features prevails, and in the intermediate positions of the control input organ a combination of the two image appearance features is generated, which combination has different ratio of the said image appearance features as a function of the position of the control input organ between the two extreme end positions.

29. A method according to claim 26 in which each standard workflow setting parameter of the combination defining an image appearance feature control parameter is related to the image appearance feature control parameter by a function which may be different for each of the said standard workflow setting parameters of the said combination.

30. A method according to claim 26 comprising the steps of generating a multidimensional space of standard setting parameters, having the number of dimensions corresponding to the number of the different standard setting parameters;

the said multidimensional space being defined by a corresponding multidimensional array of data of the values of the said standard setting parameters and the combination of the said values in relation to the different image appearance features;

defining each image appearance feature control parameter as a sub-space contained in the said multidimensional space having a reduced number of dimensions each one corresponding to an image appearance feature control parameter;

the said sub space being determined by the combination of standard workflow setting parameters influencing the image feature appearance associated with an image appearance feature control parameter and consisting in the sub array of the multidimensional array comprising the values of the said standard workflow setting parameters of the said combination of standard workflow setting parameters influencing the image appearance feature associated with an image appearance feature control parameter.

31. A method according to claim 6, wherein, when a variation of the value of an image appearance feature control parameter is carried out for obtaining a variation of the image appearance feature variation relatively to the corresponding appearance feature, the values of each of the said standard workflow setting parameters of the combination influencing the said image appearance feature control parameter are varied independently with respect to each other according to their corresponding function.

32. A method according to claim 29, wherein, when a variation of the value of an image appearance feature control parameter is carried out for obtaining a variation of the image appearance feature variation relatively to the corresponding appearance feature, the values of each of the said standard workflow setting parameters of the combination influencing the said image appearance feature control parameter are varied independently with respect to each other according to their corresponding function.

* * * * *